(12) United States Patent
Ransden et al.

(10) Patent No.: US 9,107,648 B2
(45) Date of Patent: Aug. 18, 2015

(54) TISSUE RETRACTOR ASSEMBLY

(75) Inventors: Jeffrey Ransden, Fairfield, CT (US);
Leland Ray Adams, Ansonia, CT (US);
Gregor Weaver, Waterbury, CT (US);
Vincent Mata, III, Monroe, CT (US);
Adam Lehman, Northford, CT (US)

(73) Assignee: NovaTract Surgical, Inc., Madison, CT (US)

( * ) Notice: Subject to any disclaimer, the term of this patent is extended or adjusted under 35 U.S.C. 154(b) by 313 days.

(21) Appl. No.: 13/536,548

(22) Filed: Jun. 28, 2012

(65) Prior Publication Data

US 2013/0253275 A1    Sep. 26, 2013

Related U.S. Application Data

(60) Provisional application No. 61/502,178, filed on Jun. 28, 2011.

(51) Int. Cl.
*A61B 1/32* (2006.01)
*A61B 17/02* (2006.01)
(Continued)

(52) U.S. Cl.
CPC ......... *A61B 17/0218* (2013.01); *A61B 17/0281* (2013.01); *A61B 17/0401* (2013.01); *A61B 17/29* (2013.01); *A61B 17/50* (2013.01);
(Continued)

(58) Field of Classification Search
CPC ........... A61B 1/32; A61B 2017/00283; A61B 2017/00358; A61B 17/0218; A61B 17/0281; A61B 2017/0287; A61B 17/29
USPC ............ 600/201, 204, 206, 217; 606/75, 139, 606/142, 205, 232
See application file for complete search history.

(56) References Cited

U.S. PATENT DOCUMENTS 1,741,457 A    12/1929    Glass
4,192,315 A    3/1980    Hilzinger et al.
(Continued)

FOREIGN PATENT DOCUMENTS

CA        1316430       4/1993
CN        101401720     4/2009
(Continued)

OTHER PUBLICATIONS

PCT Application No. PCT/US2012/044683, International Search Report dated Feb. 1, 2013.
(Continued)

*Primary Examiner* — Larry E Waggle, Jr.
(74) *Attorney, Agent, or Firm* — Kane Kessler, P.C.; Barry E. Negrin

(57) ABSTRACT

An intracorporeal surgical tissue retractor is provided having an anchor selectively deployable in a first tissue not to be retracted and a grasper selectively deployable on a second tissue to be retracted. A longitudinally selectively movable support is threadable through the anchor and attached at a substantially distal end of the movable support to the grasper. A deployment user interface is couplable to the movable support and has a proximal end manipulable by a user extracorporeally and a distal end releasably attachable to both the anchor and the grasper, adapted to intracorporeally deploy the anchor into the first tissue and the grasper onto the second tissue. The user interface includes a first actuator having an anchor positioning tool enabling selective deployment of the anchor in the first tissue, and a second actuator enabling selective opening and closing of the jaws of the grasper.

25 Claims, 35 Drawing Sheets

(51) Int. Cl.
*A61B 17/04* (2006.01)
*A61B 17/29* (2006.01)
*A61B 17/50* (2006.01)
A61B 17/08 (2006.01)
A61B 17/10 (2006.01)
A61B 17/00 (2006.01)

(52) U.S. Cl.
CPC .. *A61B1/32* (2013.01); *A61B 17/08* (2013.01); *A61B 17/083* (2013.01); *A61B 17/10* (2013.01); *A61B 2017/00283* (2013.01); *A61B 2017/00358* (2013.01); *A61B 2017/00867* (2013.01); *A61B 2017/0287* (2013.01); *A61B 2017/0409* (2013.01); *A61B 2017/0414* (2013.01); *A61B 2017/0427* (2013.01); *A61B 2017/0437* (2013.01); *A61B 2017/0438* (2013.01); *A61B 2017/0445* (2013.01); *A61B 2017/0464* (2013.01); *A61B 2017/0496* (2013.01)

(56) References Cited

U.S. PATENT DOCUMENTS

| | | | |
|---|---|---|---|
| 4,484,581 A | 11/1984 | Martin et al. | |
| 4,637,395 A | 1/1987 | Caspar et al. | |
| 4,854,317 A | 8/1989 | Braun | |
| 5,242,456 A | 9/1993 | Nash et al. | |
| 5,337,736 A | 8/1994 | Reddy | |
| 5,466,243 A | 11/1995 | Schmieding et al. | |
| 5,496,333 A | 3/1996 | Sackier et al. | |
| 5,514,666 A | 5/1996 | Cerda et al. | |
| 5,702,411 A | 12/1997 | Back et al. | |
| 5,733,295 A | 3/1998 | Back et al. | |
| 5,830,221 A | 11/1998 | Stein et al. | |
| 5,921,996 A | 7/1999 | Sherman | |
| 6,210,419 B1 | 4/2001 | Mayenberger et al. | |
| 6,251,117 B1 | 6/2001 | Kringel et al. | |
| 6,261,303 B1 | 7/2001 | Mayenberger et al. | |
| 6,273,898 B1 | 8/2001 | Kienzle et al. | |
| 6,358,196 B1 | 3/2002 | Rayman | |
| 6,364,887 B1 | 4/2002 | Dworschak et al. | |
| 6,440,061 B1 | 8/2002 | Wenner et al. | |
| 6,837,895 B2 | 1/2005 | Mayenberger | |
| 7,077,851 B2 | 7/2006 | Lutze et al. | |
| 7,270,672 B1 | 9/2007 | Singer | |
| 7,691,103 B2 | 4/2010 | Fernandez | |
| 8,038,612 B2 | 10/2011 | Paz | |
| 2002/0049367 A1 | 4/2002 | Irion et al. | |
| 2004/0034345 A1 | 2/2004 | Lentz | |
| 2004/0050395 A1 | 3/2004 | Ueda et al. | |
| 2004/0097982 A1 | 5/2004 | Jugenheimer et al. | |
| 2004/0111100 A1 | 6/2004 | Benderev et al. | |
| 2004/0254427 A1* | 12/2004 | Fowler, Jr. | 600/210 |
| 2005/0203344 A1 | 9/2005 | Orban, III et al. | |
| 2005/0251157 A1 | 11/2005 | Saadat et al. | |
| 2005/0251207 A1 | 11/2005 | Flores et al. | |
| 2005/0273119 A1 | 12/2005 | Widomski et al. | |
| 2006/0149135 A1 | 7/2006 | Paz | |
| 2006/0217681 A1 | 9/2006 | Hart et al. | |
| 2008/0027476 A1 | 1/2008 | Piskun | |
| 2009/0043246 A1 | 2/2009 | Dominguez | |
| 2009/0125038 A1 | 5/2009 | Ewers et al. | |
| 2009/0131749 A1 | 5/2009 | Ahmed et al. | |
| 2009/0222025 A1 | 9/2009 | Catanese, III et al. | |
| 2009/0247992 A1 | 10/2009 | Shalon et al. | |
| 2009/0312598 A1 | 12/2009 | Schaller | |
| 2009/0326518 A1 | 12/2009 | Rabin | |
| 2010/0081875 A1 | 4/2010 | Fowler et al. | |
| 2010/0081880 A1 | 4/2010 | Widenhouse et al. | |
| 2010/0094227 A1 | 4/2010 | Albrecht et al. | |
| 2010/0145361 A1 | 6/2010 | Francischelli et al. | |
| 2010/0174150 A1 | 7/2010 | Park et al. | |
| 2010/0286473 A1 | 11/2010 | Roberts | |
| 2010/0318105 A1* | 12/2010 | Jayant | |
| 2011/0087244 A1 | 4/2011 | Weisshaupt et al. | |
| 2011/0282159 A1* | 11/2011 | Galvani | 600/217 |
| 2013/0172682 A1* | 7/2013 | Ransden et al. | 600/204 |

FOREIGN PATENT DOCUMENTS

| | | | |
|---|---|---|---|
| JP | 2005-103107 | 4/2005 | |
| WO | 93/18712 | 9/1993 | |
| WO | 2005104927 | 11/2005 | |
| WO | 2007136683 | 11/2007 | |
| WO | 2008045940 | 4/2008 | |
| WO | 2009023136 | 2/2009 | |
| WO | WO 2009023136 A2 * | 2/2009 | A61B 17/00 |
| WO | 2010042913 | 4/2010 | |
| WO | 2012/006153 A1 | 1/2012 | |

OTHER PUBLICATIONS

Romanelli et al., Single Port Laparoscopic Cholecystectomy With the Triport System: A Case Report, Surgical Innovation, vol. 15, No. 3, pp. 223-228, Sep. 2008.

Choi et al., Emerging Technologies—Single-Incision Laparoscopic Surgery: How and Why?, Bariatric Times, Apr. 2009.

Dominguez et al., Retraction and Triangulation With Neodymium Magnetic Forceps for Single-Port Laparoscopic Cholecystectomy, Surg. Endosc., vol. 23, pp. 1160-1666, May 2009.

Chow et al., Single-Incision Laparoscopic Surgery for Cholecystectomy: An Evolving Technique, Surg. Endoc., vol. 24, pp. 709-714, Aug. 2009.

Single Port Approach to Surpass 20% of all Laparoscopic Procedures by 2014, PR Newswire, Dec. 1, 2009.

Raman et al., Role of Magnetic Anchors During Laparoendoscopic Single Site Surgery and Notes, Journal of Endourology, vol. 23, No. 5, pp. 781-786, May 2009.

European Patent Appln. No. 12803855.1, European Search Report dated Feb. 12, 2015.

* cited by examiner

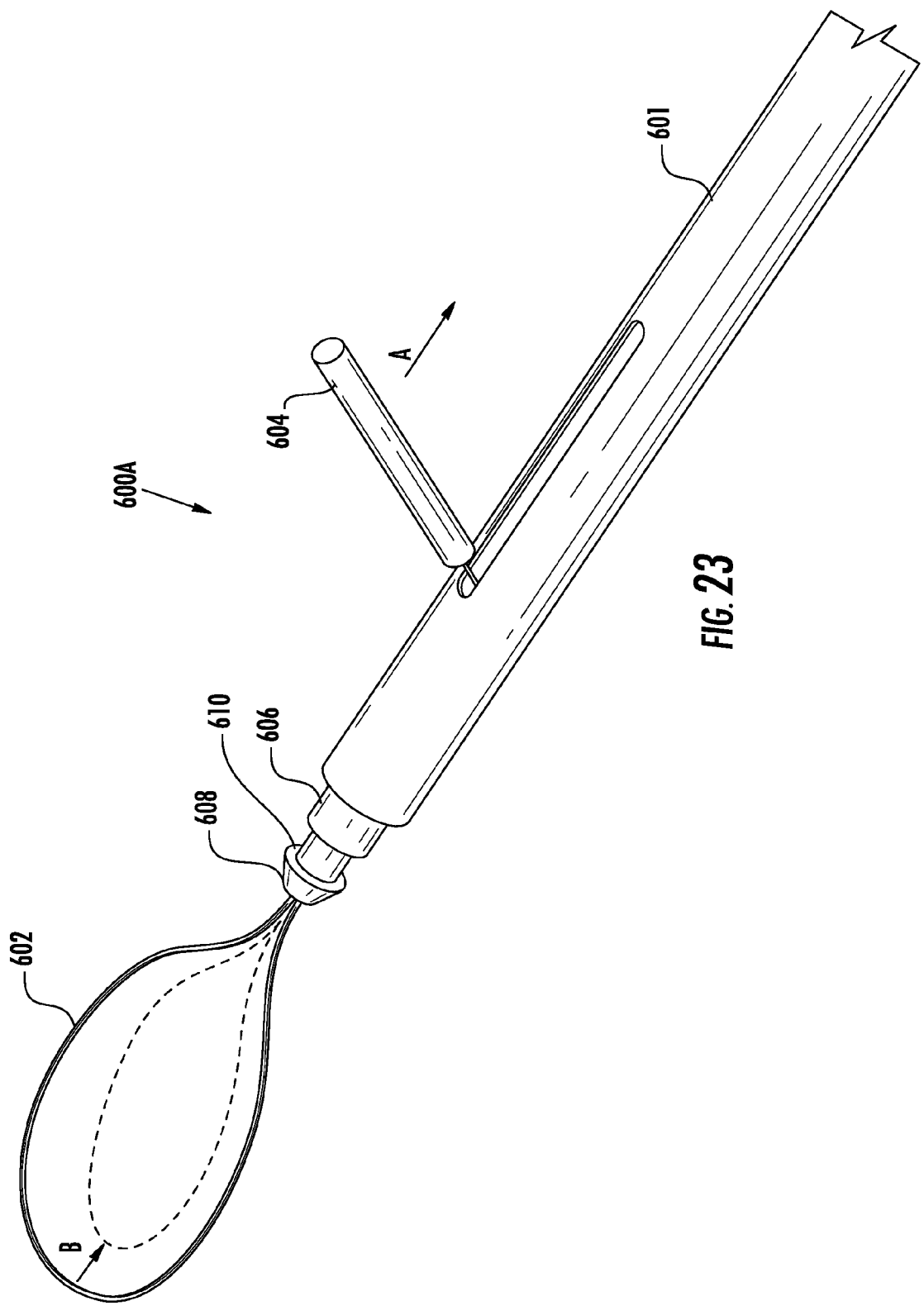

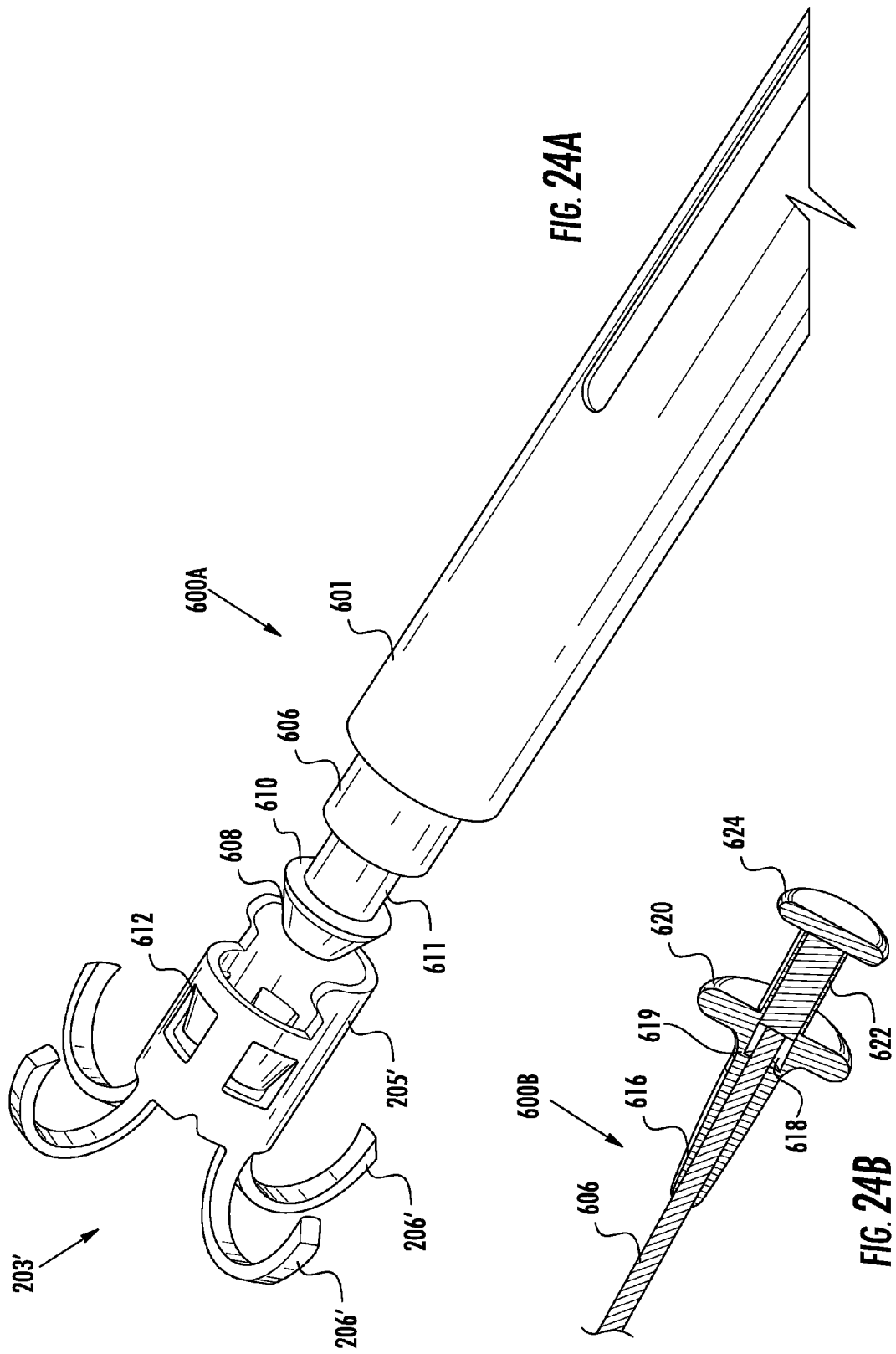

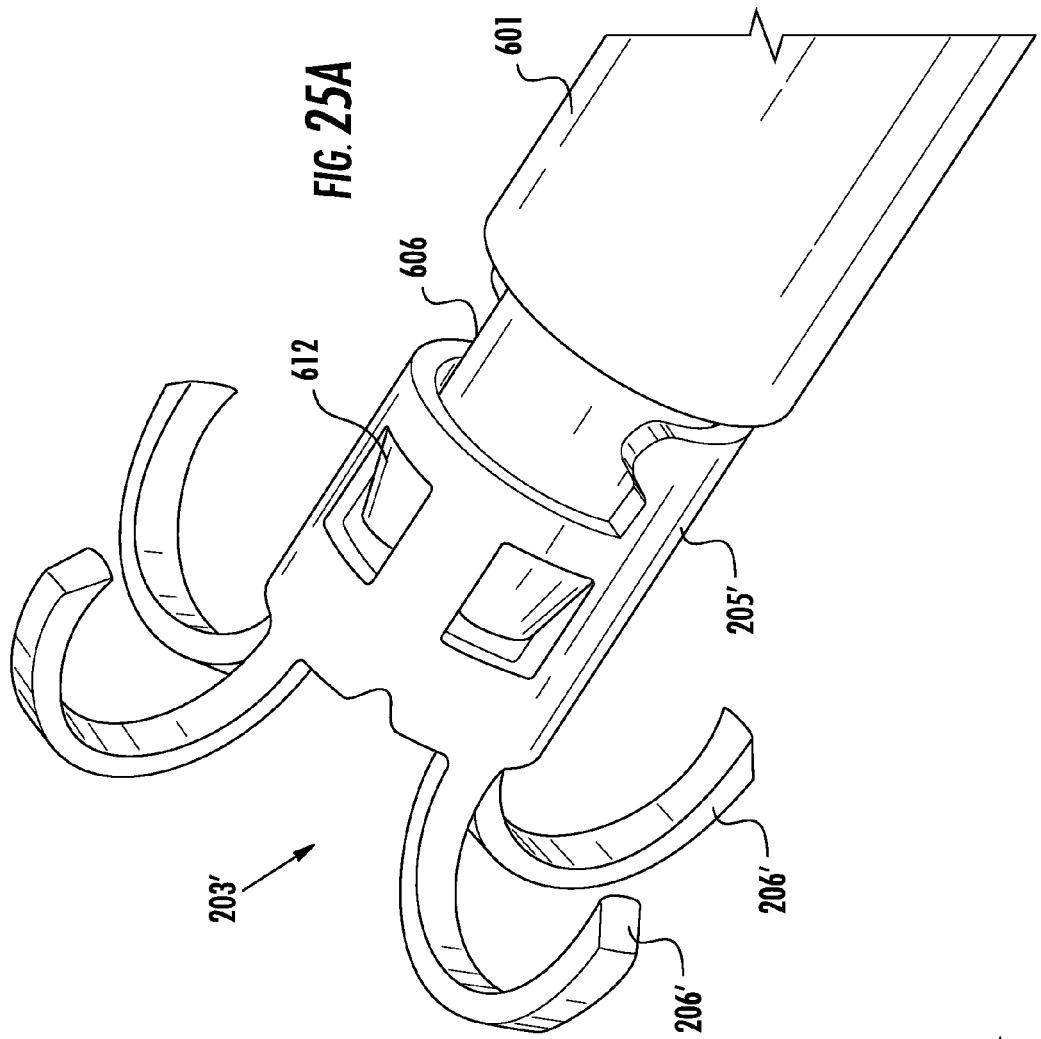
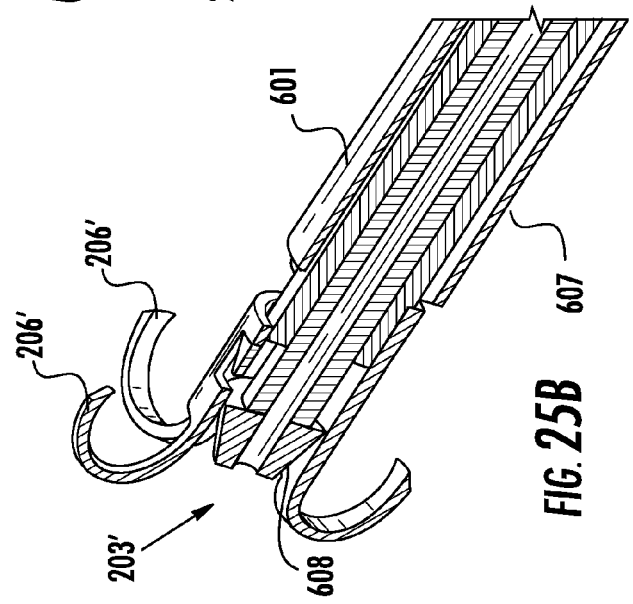

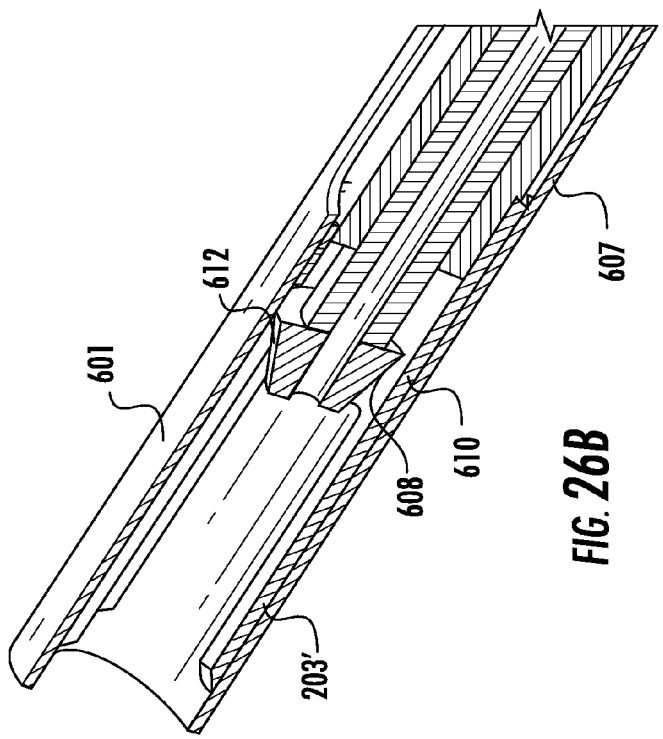
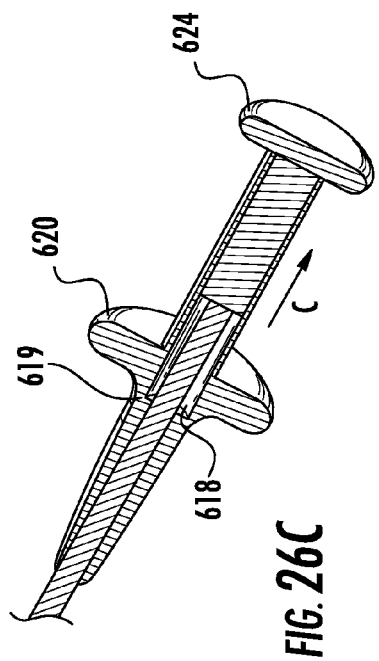
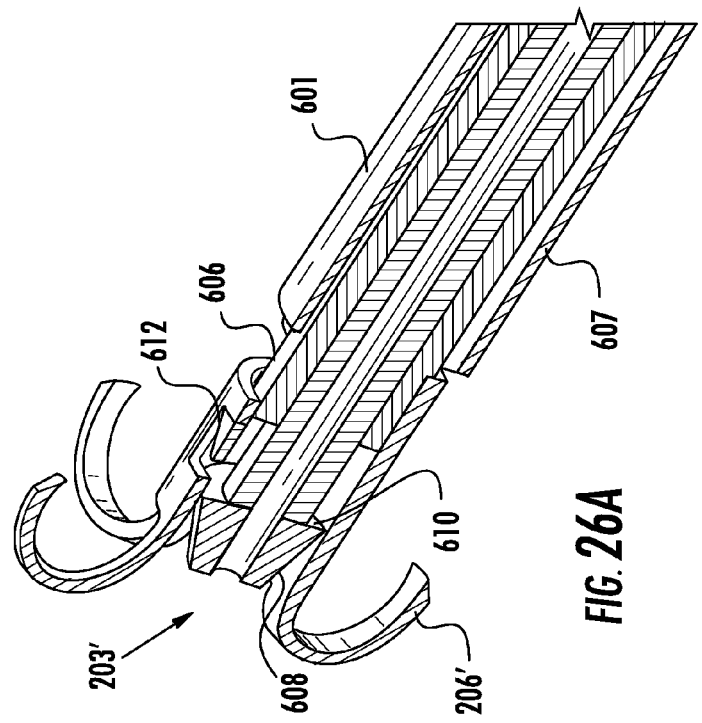
FIG. 26A
FIG. 26B
FIG. 26C

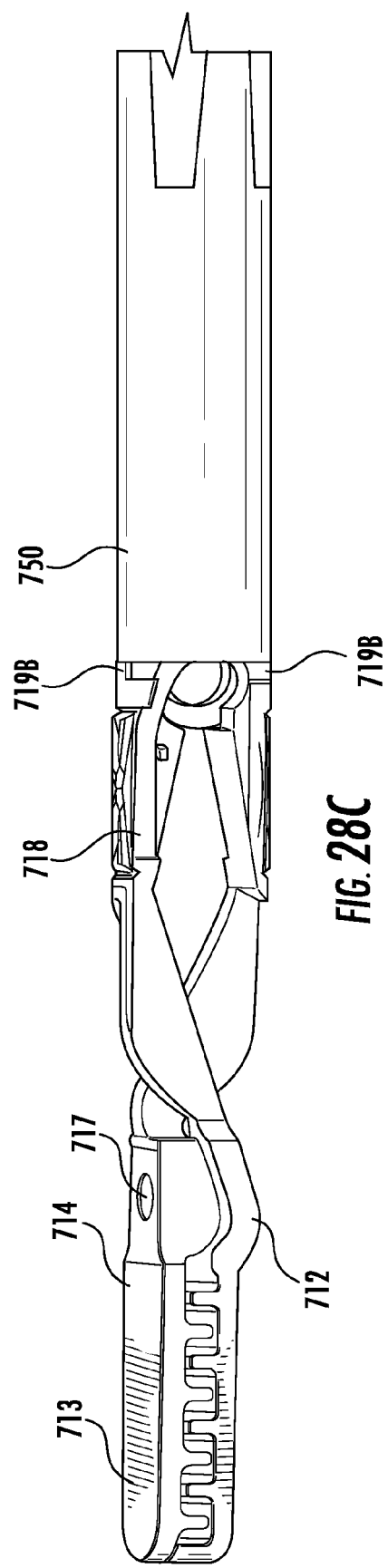

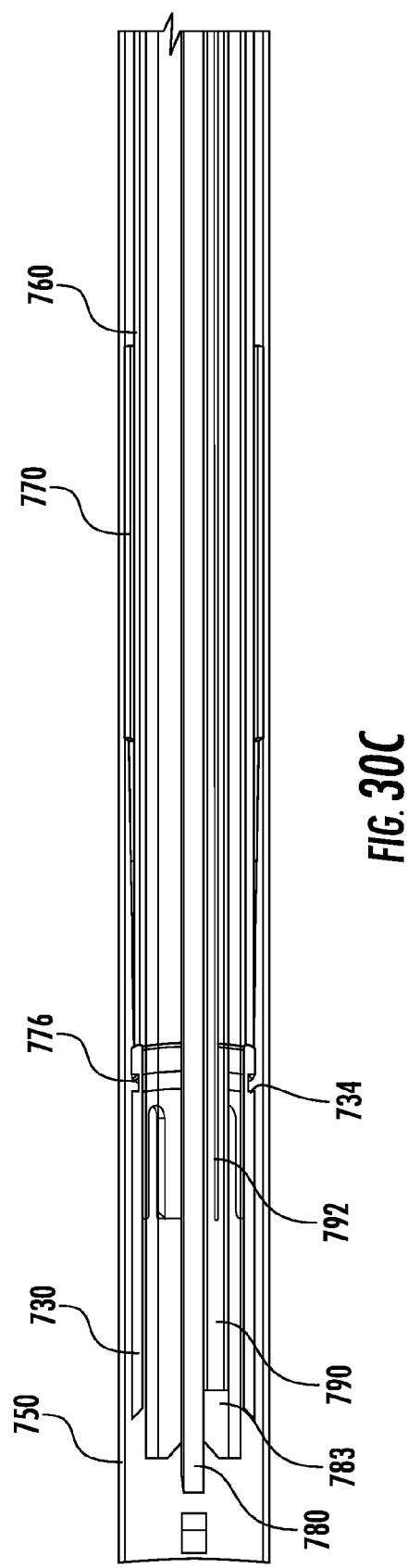

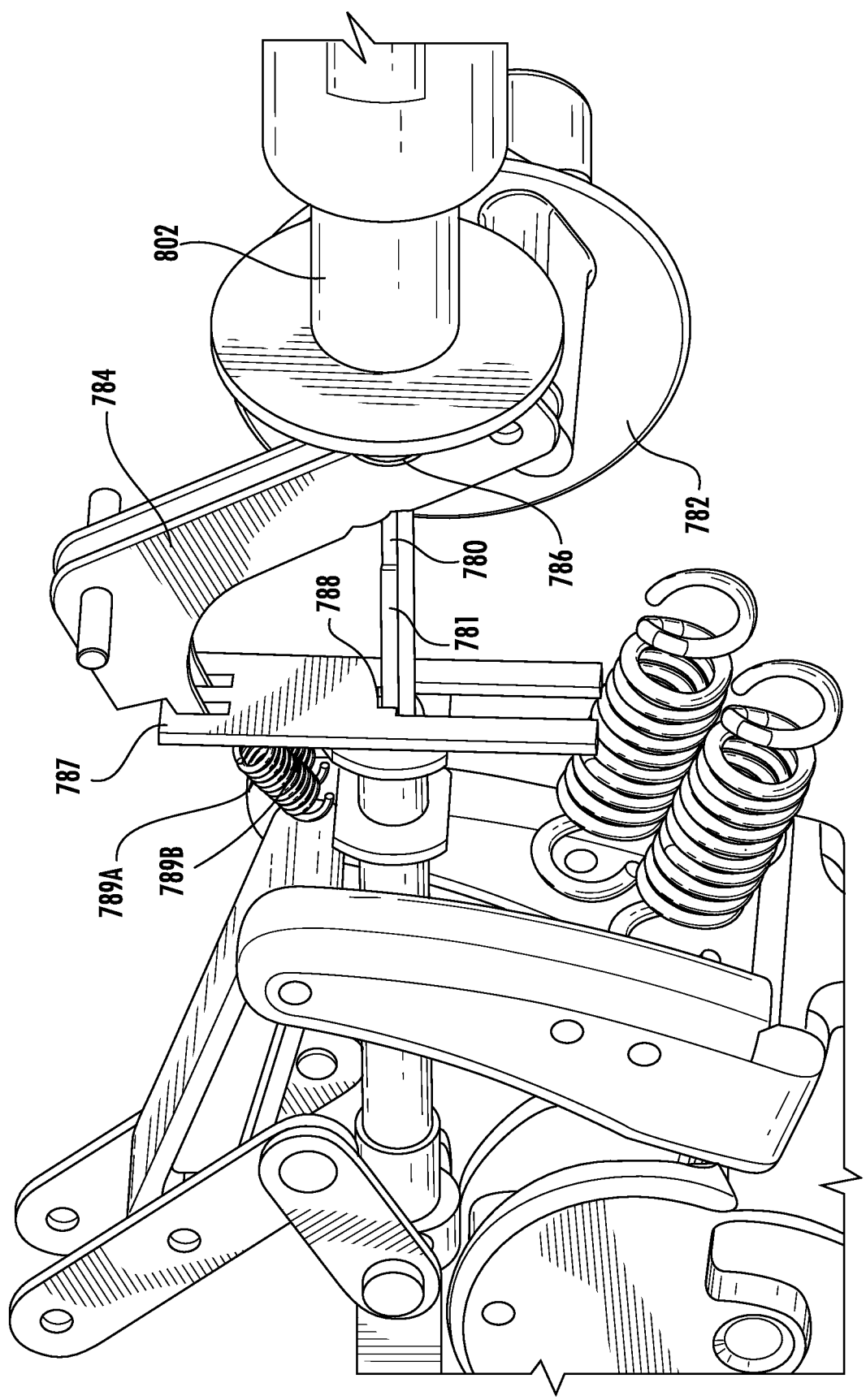

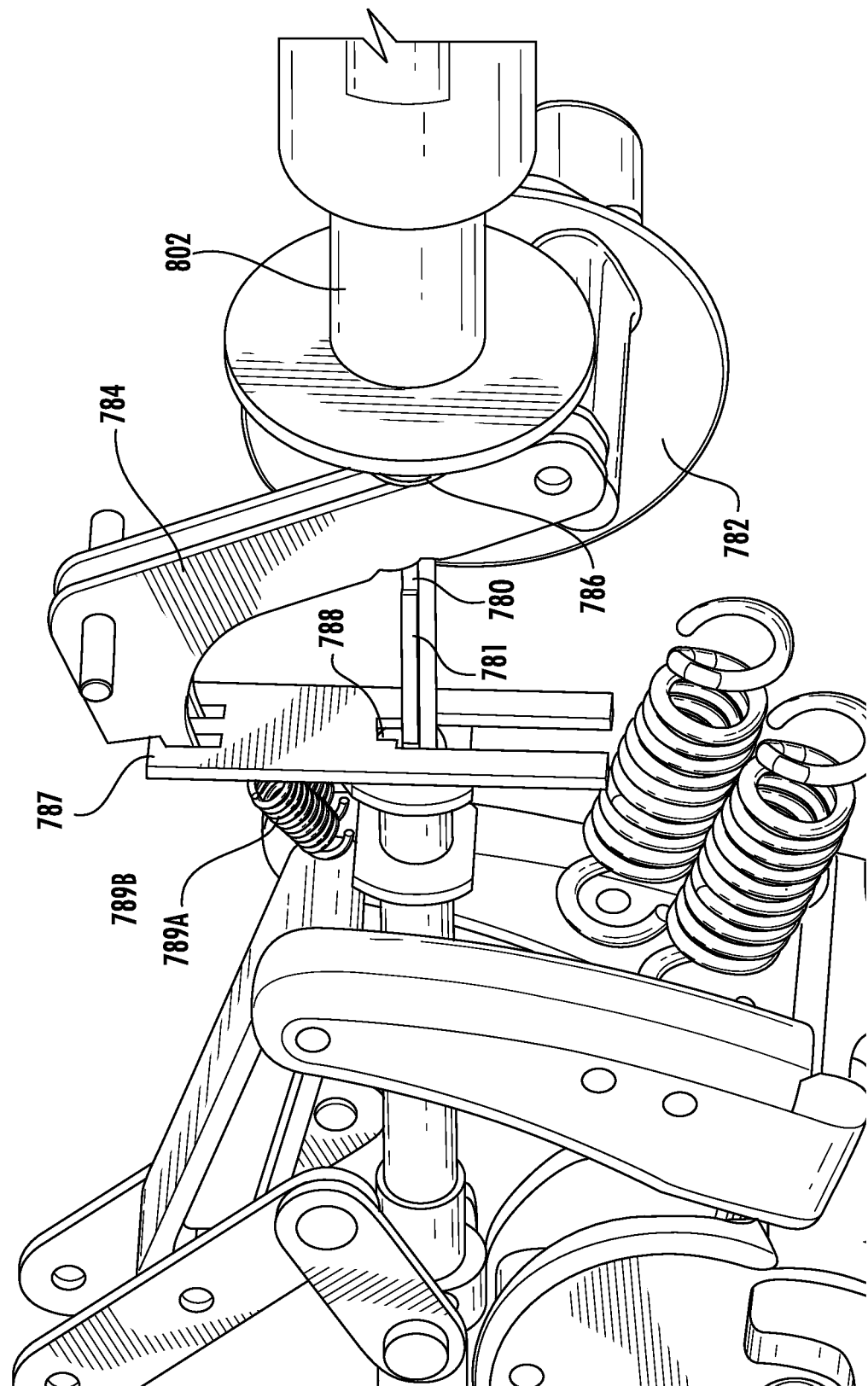

TISSUE RETRACTOR ASSEMBLY

RELATED APPLICATIONS

Priority is claimed from U.S. Provisional Patent Application No. 61/502,178 filed Jun. 28, 2011 entitled "Tissue Retractor Assembly", the teachings of which are incorporated by reference herein.

BACKGROUND OF THE INVENTION

1. Field of the Invention

The invention is directed generally to tissue retractor assemblies and, more particularly, to tissue retractor assemblies for single incision laparoscopic surgery.

2. Description of Related Art

Single port laparoscopic surgery is a surgical procedure that may provide fewer risks, less patient trauma and/or reduced surgical time. In a typical single port procedure, a single port is introduced through the umbilicus, for example, to gain access to internal organs and/or desired anatomical region(s). Retraction of the gall bladder or other organs is generally required during single port procedures. However, retraction is difficult with single port access because the port location is often caudal to the organs and provides limited access for an additional retraction instrument.

Thus, a need exists for an organ retraction system for both single port and reduced port surgery (e.g., surgeries of the gall bladder, appendix, or colon; bariatric surgeries, hysterectomies, etc.) that may be delivered in a minimally invasive manner, e.g., through one or more 5 mm (or larger) laparoscopic ports, without requiring additional abdominal incision (s) to facilitate introduction of the organ retraction system. A further need exists for an organ retraction system that is atraumatic, e.g., reducing the risk of organ damage and/or puncture in connection with tissue engagement and/or retraction. Reduction in such risks is important because, inter alia, organ trauma and/or puncture may cause infection, e.g., release of bile from the gall bladder may cause infection in the peritoneal space and increase patient risk. An additional need exists for an organ retraction system for single or reduced port surgery wherein the tension or traction of the organ can be adjusted during the procedure extracorporeally, e.g., without removing and/or reintroducing the delivery device. Still further, a need exists for an organ retraction system which can grasp varied anatomical presentations of target organs. These and other needs are addressed by the assemblies of the present disclosure.

SUMMARY OF THE INVENTION

In accordance with embodiments of the present disclosure, tissue retractor assemblies are disclosed that are particularly advantageous for use in single or reduced port laparoscopic surgical procedures or similar operations. Generally, the disclosed tissue refractor assemblies are laparoscopic surgical assist devices which facilitate the retraction of various organs and/or structures intracorporeally. In exemplary embodiments, the tissue retractor is a multi-component device configured and dimensioned to be delivered through a 5 mm (or larger) laparoscopic or similar port(s) and provides an atraumatic means to grasp and hold an organ or other anatomical structure, e.g., the gall bladder.

In accordance with embodiments of the present disclosure, exemplary tissue retractor assemblies are disclosed which are adapted to retract an organ or other anatomical structure through cooperative interaction between an atraumatic grasper and an anchored guide member/suture subassembly, e.g., a suture that passes through an anchor positioned or otherwise secured with respect to a fixed position (e.g., the abdominal wall). More particularly, the disclosed tissue retractor assemblies may function by (i) placing or securing an anchor with respect to an anatomical structure, e.g., the abdominal wall, (ii) associating a suture with the anchor (either before or after securing the anchor with respect to the anatomical structure), (iii) engaging, attaching and/or securing a deployable atraumatic grasper with respect to an organ, tissue or other anatomical structure, and (iv) managing/manipulating the suture that is attached or otherwise secured with respect to the grasper and routed through the anchor, thereby allowing the organ/tissue/anatomical structure to be retracted, moved or otherwise manipulated, e.g., by tensioning the suture. Of note, the suture is advantageously passed through the abdominal wall, e.g., through a port, and is generally manipulated by a surgeon/user from such external location.

In exemplary implementations, the tissue retractor assembly is adapted for introduction and use through an abdominal wall, e.g., through a 5 mm port, and includes a cannula that defines an axis and a distal end. A grasper and an anchor are detachably secured with respect to the distal end of the cannula. A suture is cooperatively associated with the grasper and the anchor for movement/manipulation of the grasper relative to the anchor. The grasper generally is configured and dimensioned to be extended axially from the cannula, and includes first and second legs/jaws for gripping an organ, tissue and/or other structure. The grasper further includes a tubular member that is axially movable so as to move the legs/jaws of the grasper relative to each other, e.g., through a cinching or camming action. The tubular member may function as or otherwise cooperate with a locking mechanism that is configured and dimensioned to be advanced/pushed distally to grasp and lock the first and second leg/jaw in engagement with a target structure, e.g., organ, tissue, and/or other structure.

The anchor generally is configured and dimensioned to be deployed from the distal end of the cannula. The anchor may be advantageously secured relative to an anatomical location/structure within the abdominal cavity, e.g., the anchor may be attached to an abdominal wall adjacent to an organ, tissue or other structure of interest. The anchor is generally defined by a body, e.g., a cylindrical body, and at least two sharpened legs that extend relative thereto. Preferably, the anchor includes more than two legs; more preferably, the anchor includes four such legs. The sharpened legs may advantageously be adapted to be positioned along the axis of the cannula (or substantially along such axis), e.g., to facilitate introduction through the abdominal wall. In exemplary embodiments, the sharpened legs are fabricated from a resilient material, e.g., nitinol or stainless steel, and formed/shaped so as to resiliently move between first and second positions/configurations. More particularly, the legs are advantageously fabricated so as to move between a first, relatively straight, substantially axially-aligned configuration (e.g., during abdominal introduction) and second, curved configurations (e.g., after deployment through the cannula within the abdominal cavity) to provide suitable anchoring. Thus, the at least two legs (and preferably four legs) may automatically deploy into the abdominal wall, e.g., in a substantially crossing configuration or, in the case of the preferred embodiment, in an outwardly curved configuration, to effect fixation of the anchor relative to the abdominal wall. The sharpened ends of the legs facilitate tissue penetration and the preferably outwardly curved configuration of the legs upon deployment resists unintentional withdrawal of the anchor from the abdominal wall. According to the present disclosure, a suture may be introduced to the abdominal cavity, e.g., through the cannula, and passed through (i) the body of the anchor (or through an extension associated with the body) and (ii) a cooperative aspect of the grasper. Typically, the suture is pre-associated with the grasper and anchor before abdominal introduction. The suture may be manipulated by the surgeon/user from a position external to the abdominal cavity and, based upon passage through the anchor, a desired level of tension and/or directional force may be delivered to the grasper. Thus, in exemplary implementations, the position of the grasper relative to the anchor may be remotely adjusted through suture manipulation, e.g., by introducing an additional length of suture to the abdominal cavity or withdrawing a length of suture from the abdominal cavity.

The disclosed tissue retractor assembly, therefore, includes an anchor which provides a robust attachment to a desired substrate, e.g., a peritoneal structure associated with the abdominal wall, that is not possible with non-piercing anchors. In addition, the disclosed tissue retractor assembly may be used to transfer a force to a grasper positioned within the abdominal cavity, e.g., through manipulation of a length of suture or fiber that extends from the abdominal cavity, thereby enabling a surgeon/user to tension and/or reposition the grasper relative to a substantially fixed point defined by the anchor. In exemplary implementations, the suture/fiber passes through a port to effectuate and/or support minimally invasive surgical procedures. The disclosed assembly thus enables introduction and manipulation of an advantageous grasper through a minimally invasive point of access, e.g., a 5 mm port.

In accordance with further embodiments of the present disclosure, the first and second legs/jaws of the grasper are fabricated from stainless steel or other material providing the requisite strength/resilience. The legs/jaws are generally formed into a desired initial shape. At least one of the first and second legs/jaws of the grasper may further include serrations on a distal end thereof in order to better grasp and/or capture tissue. Additionally, one of the first and second legs/jaws may further define an angled or arcuate portion that enables the grasper to be opened sufficiently widely to facilitate grasping of an organ, tissue and/or other desired anatomical element. The locking mechanism associated with the grasper may be defined by a ring-shaped member or, more preferably, an elongated and/or short tubular member which is configured and dimensioned to be pushed or otherwise advanced distally relative to the grasper so as to pass over/around proximal portions of the first and second legs/jaws, thereby causing the first and second legs/jaws to clinch shut over the tissue, organ or other anatomical structure, e.g., through a camming action effectuated by the distally advancing ring/tubular member.

In accordance with further embodiments of the present disclosure, one or both of the first and second legs/jaws of the grasper may include a rubber or other coating applied to the distal ends thereof (in whole or in part) in order to better grasp and capture tissue in an atraumatic manner.

In accordance with further embodiments of the present disclosure, an exemplary tissue retractor assembly is disclosed that is adapted to (i) fire an anchor with a retractable sharp tip and retractable barbs into an abdominal wall or other anatomical structure, (ii) deploy a wire form to grasp an organ or other structure to be retracted or otherwise manipulated, and (iii) facilitate management of a suture that is attached or otherwise secured relative to the wire form and is routed through the anchor, thus allowing the organ/structure to be retracted or manipulated by tensioning the suture. Specifically, an exemplary tissue retractor assembly includes a cannula which is configured and dimensioned to house or otherwise detachably secure an anchor, a wire form and optionally a grasper. The anchor is configured and dimensioned to be deployed from the cannula and attached relative to an abdominal wall adjacent to an organ or other structure of interest, e.g., anterior thereto.

The anchor may be defined by an outer tube and a central shaft, and may further include at least two barbs which are configured to be deployed when the central shaft is pulled axially. The wire form may be defined by a coiled spring configured and dimensioned to deploy out of a distal end of the cannula and expand radially, whereby the wire form may be secured and adjusted relative to the anchor by a length of suture or other fiber. In accordance with further embodiments of the present disclosure, the wire form further includes surface roughness or barbs along the interior surface of the wire form to enhance the gripping of tissue. A grasper may be provided that is configured and dimensioned to extend out of the distal end of the cannula and through the wire form, such grasper being effective to grasp tissue and retract it into the wire form.

The disclosed tissue retractor assembly, therefore, while utilizing known medical technologies and current laparoscopic techniques, advantageously provides an anchor which may be used to transfer a force that is delivered from a position external to the abdominal cavity. The force may be delivered through manipulation of a length of suture or fiber relative to the anchor, thereby allowing the surgeon/user to tension or otherwise manipulate a grasper positioned within the abdominal cavity. Indeed, according to the present disclosure, a surgeon may manipulate a grasper relative to an anchor point established in the peritoneal wall or other location within the abdominal cavity.

In accordance with embodiments of the present disclosure, an exemplary tissue retractor assembly is disclosed which may function to deploy a suture around an organ or other anatomical structure, e.g., in a looping manner. The tissue retractor assembly may further be adapted to (i) fire an anchor with an angled sharp tip into an abdominal wall, and (ii) manage a suture that is attached to the loop of suture and routed through the anchor, thus allowing the organ/structure to be retracted by tensioning the suture, e.g., through a port that passes through the abdominal wall. Specifically, the exemplary tissue retractor assembly includes a cannula which houses an anchor and a grasper. The grasper is defined by a loop of suture with a one way locking toggle that is configured and dimensioned to be released/advanced distally from the cannula, the loop of suture being configured and dimensioned to grasp an organ or other anatomical structure, and to retract and tighten around the organ/structure.

In accordance with further embodiments of the present disclosure, the loop suture may include small cuts or barbs to increase the friction of the loop of suture relative to the organ, thereby reducing the possibility of slippage therebetween. The one way locking toggle may be defined by a molded plastic part which allows the loop of suture to be pulled through in one direction, but stops the loop of suture from loosening. Additionally, the anchor may be defined by a substantially symmetrical structure.

The anchor may be defined by a back span, torsion springs and an axial connection between the back span and torsion springs. The anchor may further include two sharpened legs configured and dimensioned to deploy from a distal end of the cannula. The grasper may be adjusted and/or manipulated relative to the anchor by a length of suture that passes therethrough. The disclosed tissue retractor assembly, therefore, while utilizing known medical technologies and current laparoscopic techniques, provides a spring clip anchor which allows penetration of the abdominal tissue with a reduced chance for clinical injury and may be used to transfer a force from a location external to the abdominal cavity. A length of suture or fiber may be used to enable tensioning of the organ grasper, such suture/fiber passing through the anchored point and ultimately passing through the abdominal wall, e.g., through a port. The disclosed delivery system may advantageously facilitate introduction through a 5 mm port, and permit interaction with both the grasper and the anchor to achieve the clinical results described herein. The disclosed system also generally facilitates management and routing of the suture from the delivery port and permits/facilitates removal of the clip from the abdominal wall.

In accordance with embodiments of the present disclosure, an exemplary tissue retractor assembly is disclosed which fires sequentially deployed 5 mm Raney clips. The Raney clips may be adapted to exit the end of the cannula and are therefore fired axially as opposed to the traditional transverse method. The Raney clip may be atraumatically applied to an organ or structure according to the present disclosure and a second clip may be applied which functions as an anchor in the abdominal wall. A suture may be attached to a grasper and routed through the second clip/anchor, thus allowing the organ/structure to be retracted by tensioning the suture, e.g., from an external location based on the suture passing through the abdominal wall, e.g., through a port.

Specifically, in exemplary embodiments, the tissue retractor assembly may include a cannula which houses a first grasper and a second grasper. The first grasper is defined by a first clip configured and dimensioned to be deployed axially from a distal end of the cannula, and is further defined by a C-shaped form after deployment from the cannula. The second grasper is defined by a second clip configured and dimensioned to be deployed axially from a distal end of the cannula, and is further defined by a C-shaped form after deployment from the cannula. The first grasper is advantageously adapted to be secured and adjusted relative to the second grasper by a length of suture.

In accordance with further embodiments of the present disclosure, the first clip and second clip are metal, plastic or a combination of metal and plastic. The first clip and second clip are further defined by teeth at an open tip or on an inside surface of the first clip and second clip to aid in gripping tissue. The first clip and second slip may further include rubber coating to aid in atraumatically grasping tissue.

The disclosed tissue retractor assembly, therefore, provides both organ and anchor attachment with the same type of clip and deployment technique. The disclosed retractor assembly thus allows the possibility of deployment of multiple clips if advantageous to the procedure, an anchor which may be used to transfer a force, a length of suture or fiber to enable tensioning from the organ grasper through the anchored point, and a delivery system to enable introduction through a 5 mm port. The disclosed system permits attachment/securement of both the grasper and the anchor within the abdominal cavity and permits the surgeon/user to manage/manipulate the grasper through interaction with a suture that passes through the abdominal wall, e.g., through a delivery port. Moreover, the disclosed tissue refractor assembly permits removal of the clip/anchor from the abdominal wall on an as-desired basis.

Additionally, an anchor retrieval tool is contemplated as being part of the inventive tissue retraction assembly. A locator loop projects from the end of the tool and serves to enable easy location of the anchor in the body. The locator loop is looped around the suture that is attached to the anchor 203, and the retrieval tool is guided along the suture directly to the anchor. Disposed within the main body of the retrieval tool is a central shaft, the distal end of which includes a sloped portion that terminates in a shoulder or flange. The shoulder preferably interacts with at least one (and preferably more than one) flexible detent tabs cut into and angled inwardly towards the center of the cylindrical body of the anchor. When the distal end of the central shaft enters the interior of the anchor, the tabs catch underneath the shoulder or flange of the central shaft, thereby preventing removal of the anchor from the distal end of the shaft.

In accordance with the invention, an intracorporeal surgical tissue retractor is provided, having a) an anchor selectively deployable in a first tissue not to be retracted; b) a grasper selectively deployable on a second tissue to be retracted; c) a longitudinally selectively movable support threadable through the anchor and attached at a substantially distal end of the movable support to the grasper; and d) a deployment user interface, couplable to the movable support and having a proximal end manipulable by a user extracorporeally and a distal end releasably attachable to both the anchor and the grasper, adapted to intracorporeally deploy the anchor into the first tissue and the grasper onto the second tissue. When the anchor is deployed in the first tissue, the grasper is deployed on the second tissue, and the movable support is selectively moved proximally, the second tissue is selectively retracted. The more the movable support is selectively moved proximally, the more the second tissue is retracted, thereby enabling dynamic retraction of the second tissue.

In one embodiment, the anchor preferably includes a plurality of distally projecting legs and a substantially proximally disposed main body. Preferably, the legs of the anchor are curved outwardly and made from a resilient material. The user interface further includes an outer cannula or tube and an anchor positioning tool attached to a distal end of the user interface and relatively withdrawable inside of a distal end of the outer cannula. As the anchor positioning tool is relatively withdrawn into the outer cannula, the outer cannula urges the legs of the anchor that is releasably secured to the anchor positioning tool into a substantially straight configuration. When the legs are in the substantially straight configuration, the anchor is deployable into a tissue not to be retracted.

Preferably, an anchor positioning tool is attachable to the distal end of the user interface and releasably attachable to the main body of the anchor. One of the main body of the anchor and the anchor positioning tool includes a flange and the other of the main body of the anchor and the anchor positioning tool includes a plurality of arms releasably securable to the flange. The user interface preferably includes an outer cannula and a middle cannula disposed within the outer cannula, the anchor positioning tool being attached to a distal end of the middle cannula. In this embodiment, it is preferred that the arms be disposed on the anchor positioning tool and biased radially outwardly from the middle cannula, wherein when the middle cannula is relatively withdrawn into the outer cannula, the arms are urged radially inwardly via the outer cannula.

The legs of the anchor are preferably curved outwardly and made from a resilient shape memory material; as the middle cannula is relatively withdrawn into the outer cannula, the outer cannula urges the legs of the anchor into a substantially straight configuration. The proximal end of the user interface preferably includes a first actuator coupled to the middle cannula; actuating the first actuator in a first motion moves the middle cannula in a distal direction to enable deployment of the anchor in the first tissue. Preferably, actuating the first actuator in a second motion moves the middle cannula in a proximal direction to withdraw the anchor from the first tissue.

In one embodiment, the main body of the anchor preferably includes a shoulder region releasably attachable to an anchor positioning tool attached to the distal end of the user interface. The shoulder region includes a groove, and the anchor positioning tool includes a plurality of arms releasably securable in the groove. As above, the user interface includes an outer cannula and a middle cannula disposed within the outer cannula, the anchor positioning tool being attached to a distal end of the middle cannula. The arms of the anchor positioning tool are biased radially outwardly from the middle cannula; when the middle cannula is relatively withdrawn into the outer cannula, the arms are urged radially inwardly via the outer cannula to engage with the groove of the anchor. The main body of the anchor preferably also includes at least one notch formed at a distal end of the main body adapted to accommodate the movable support when the anchor is deployed in the first tissue.

The resilient material of the anchor is preferably variably pliant at different temperatures, wherein the material is less pliant at body temperature than at room temperature.

In one embodiment, the grasper includes a pair of arms forming at their respective distal ends a pair of jaws, the jaws adapted to securely attach to the second tissue; and a biasing mechanism attached to the arms biasing the jaws into a closed position. Preferably, the grasper further includes a pair of corresponding holes respectively formed in each of the arms through which the movable support is disposable. When the movable support is selectively moved proximally, additional force is applied to the jaws via the movable support through the holes in the grasper arms further tending to close the jaws into the closed position.

In one embodiment, as above, the user interface includes an outer tube or cannula and the grasper is at least partially relatively withdrawable into and out of the outer cannula; when at least one of the outer cannula and the grasper is moved relative to the other of the outer cannula and the grasper to cause the grasper to be at least partially withdrawn into the outer cannula, a distal end of the outer cannula bears against a proximal end of the arms of the grasper and forces the jaws open opposing the biasing mechanism. Preferably, the user interface includes a longitudinally movable outer cannula and a substantially stationary grasper support disposed within the outer cannula and attachable to the grasper, the grasper being at least partially withdrawable into and out of the outer cannula. When the outer cannula is moved relative to the grasper to cause the grasper to be at least partially withdrawn into the outer cannula, a distal end of the outer cannula bears against a proximal end of the arms of the grasper and forces the jaws open opposing the biasing mechanism.

In another embodiment, the user interface includes an outer cannula having a distal rim, and the grasper has a proximal end at least partially abuttable against the distal rim of the outer cannula. When at least one of the outer cannula and the grasper is moved relative to the other of the outer cannula and the grasper, the distal rim of the outer cannula bears against the proximal end of the grasper and forces the jaws open opposing the biasing mechanism. In this embodiment, it is preferred that the user interface include a longitudinally movable outer cannula having a distal rim and a grasper support disposed within the outer cannula and attachable to the grasper. In either case, the proximal end of the grasper preferably includes an outer diameter portion that is abuttable against the distal rim of the outer cannula; relative movement of the grasper to the outer cannula forces the jaws open via abutment of the distal rim against the outer diameter portion.

In accordance with the invention, in one embodiment, the user interface includes a first actuator, disposed on the proximal end of the user interface and mechanically coupled to the anchor positioning tool, enabling selective longitudinal movement of the anchor positioning tool and deployment of the anchor in the first tissue. The user interface preferably also includes a second actuator, disposed on the proximal end of the user interface and mechanically coupled to one of the outer cannula or the grasper, enabling selective relative longitudinal movement of the grasper with respect to the outer cannula to selectively open and close the jaws of the grasper. Preferably, the second actuator is mechanically coupled to the outer cannula enabling selective longitudinal movement of the outer cannula with respect to the grasper to selectively open and close the jaws of the grasper. The user interface preferably further includes a third actuator, disposed on the proximal end of the user interface and mechanically coupled to the grasper support enabling selective longitudinal movement of the grasper support to free the grasper of the user interface and to deploy the grasper onto the second tissue. The biasing mechanism of the grasper preferably includes a coil spring disposed at the proximal end of the grasper, and the grasper support preferably includes a hook formed at a distal end of the grasper support that is hookable through the coil spring. The hook is preferably dimensioned to fit within the main body of the anchor to facilitate retrieval of a deployed the anchor. The user interface preferably further includes a substantially immovable grip for opposability of movement of the first and/or second actuators.

Optionally, the invention includes an anchor retrieval tool having a main body and a central shaft disposed within the main body, the central shaft having a proximal end and a distal end, the distal end of the central shaft including a sloped portion terminating in a shoulder matingly engageable with at least one flexible detent tab cut into and angled inwardly towards a center of the main body of the anchor. When the distal end of the central shaft enters an interior of the main body of the anchor, the tab catches underneath the shoulder of the central shaft, thereby preventing removal of the anchor from the distal end of the central shaft and thereby facilitating retrieval of the anchor from the first tissue. The anchor retrieval tool may further include a locator loop projecting from a distal end of the main body of the tool, the locator loop being loopable around the movable support threaded through the anchor so that the retrieval tool is guidable along the movable support directly to the anchor. The locator loop is preferably coupled to a loop tightener adapted to selectively tighten the locator loop around the movable support.

Preferably, the movable support mentioned above includes a suture having a proximal end wound around and selectively unwindable from a spool disposed in the proximal end of the deployment user interface. The suture is preferably threaded through the user interface to the distal end of the user interface. The user interface preferably includes a wire locator loop selectively projectable from the distal end of the user interface and mechanically coupled to a fourth actuator disposed on the proximal end of the user interface and adapted to capture the movable support and withdraw the movable support into the user interface to enable location of the deployed anchor and the deployed grasper.

Additional features, functions and benefits of the disclosed tissue retractor assemblies will be apparent from the detailed description which follows, particularly when read in conjunction with the appended figures.

BRIEF DESCRIPTION OF THE DRAWINGS

FIG. 23 is a perspective view of the distal end of the exemplary anchor retrieval tool of FIG. 22.

FIG. 24A is a cutaway perspective view of the distal end of the exemplary anchor retrieval tool of FIGS. 22-23 in relation to an exemplary anchor in accordance with the invention.

FIG. 24B is a partial sectional view of the proximal end of the exemplary anchor retrieval tool of FIGS. 22-23.

FIG. 25A is a perspective view of the distal end of the exemplary anchor retrieval tool of FIGS. 22-24 secured onto the exemplary anchor depicted in FIG. 24A.

FIG. 25B is a sectional view of the distal end of the exemplary anchor retrieval tool in accordance with the invention of FIGS. 22-24 secured onto the exemplary anchor depicted in FIG. 24A.

FIGS. 26A-B are sectional views of the distal end of the exemplary anchor retrieval tool of FIGS. 22-25 removing the anchor from tissue (not shown).

FIG. 26C is a sectional view of the proximal end of the exemplary anchor retrieval tool of FIGS. 22-25 depicting removal of the anchor.

FIGS. 28C-D are perspective views of the tissue retractor grasper of FIGS. 28A-B interacting with a cannula in accordance with the invention.

FIG. 30C is a side sectional view of the distal end of the user interface of the tissue retractor assembly of FIGS. 27A-B with the grasper removed for clarity.

FIG. 32A-C are rear perspective views of the hook actuation assembly of the tissue retractor assembly of FIGS. 27A-B with one of the slide knobs removed for clarity.

DETAILED DESCRIPTION OF THE INVENTION AND DRAWINGS

In accordance with embodiments of the present disclosure, tissue retractor assemblies are disclosed that generally involve tissue retractors for single or reduced port laparoscopic surgery or similar operations. Specifically, the tissue retractor assemblies are laparoscopic surgical assist devices which facilitate the retraction of various organs or tissues intracorporeally. The tissue retractor assemblies generally take the form of multi-component devices configured and dimensioned to be delivered through an abdominal wall, e.g., through a laparoscopic or similar port (e.g., 5 mm), and to provide an atraumatic means to grasp and hold an organ or other anatomical tissue/structure, e.g., the gall bladder. The dimensional characteristics of the disclosed tissue retractor assemblies/systems are generally adapted for use through a 5 mm cannula commonly encountered in the use and operation of laparoscopic surgical tools.

Description will now be given with reference to the attached FIGS. 1-33. It should be understood that these figures are exemplary in nature and in no way serve to limit the scope of the invention, which is defined by the claims appearing hereinbelow.

Figure 1:
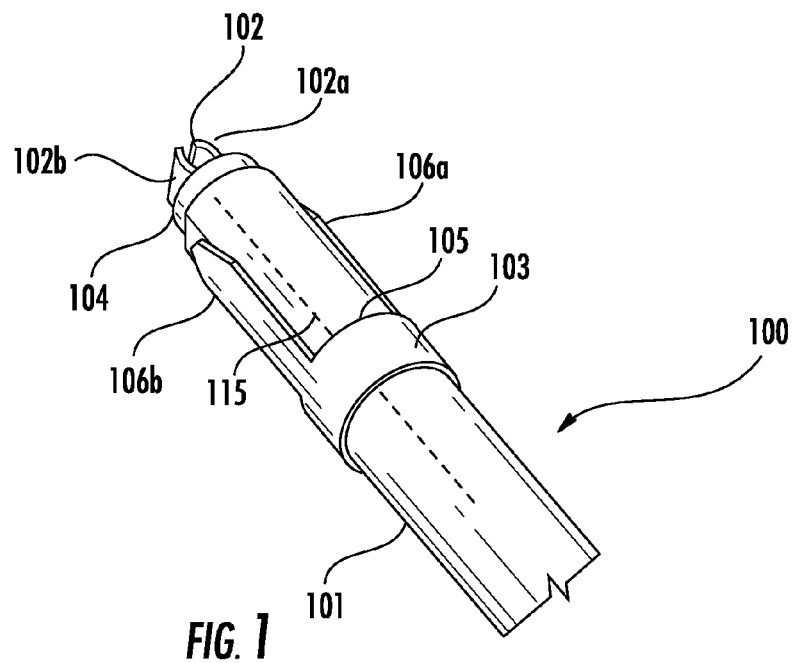
FIG. 1 is a perspective view of an exemplary tissue retractor cannula housing a grasper and anchor.

With reference to FIG. 1, an exemplary embodiment of a tissue retractor assembly is depicted in accordance with the present disclosure in the form of a tissue retractor assembly 100. The tissue retractor assembly 100 includes a tube or cannula 101 which houses a grasper 102 and an anchor 103. The grasper 102 is configured and dimensioned to be extended axially from a distal end of the cannula 101 and includes a first leg 102a and a second leg 102b for gripping tissue. The first leg 102a and second leg 102b may be fabricated from flat sheet metal or plastic. Further, first and second leg 102a and 102b may optionally be coated with a rubber, have surface features or a shape that is advantageous to grasping without damaging the organ. The grasper 102 further comprises a locking ring 104 which is configured and dimensioned to be pushed distally by an internal cannula (not shown) to grasp and lock the first leg 102a and second leg 102b around an organ or tissue. The locking ring 104 may be fabricated from a short tube or a ring-shaped member.

The tissue retractor assembly 100 further includes the anchor 103 which is configured and dimensioned to be deployed from the cannula 101 and attached to an abdominal wall anterior to an organ. The anchor 103 is further defined by a cylindrical body 105 attached to at least two sharpened thin legs, 106a and 106b, respectively, that lie along an axis 115 of the cylindrical body 103. The at least two sharpened thin legs 106a and 106b are preformed into a preformed shape that when the anchor 103 is deployed by cannula 101, the at least two sharpened thin legs 106a and 106b return to the preformed shape to increase a pull out force of the anchor 103.

Figures 2A, 2B, 2C:
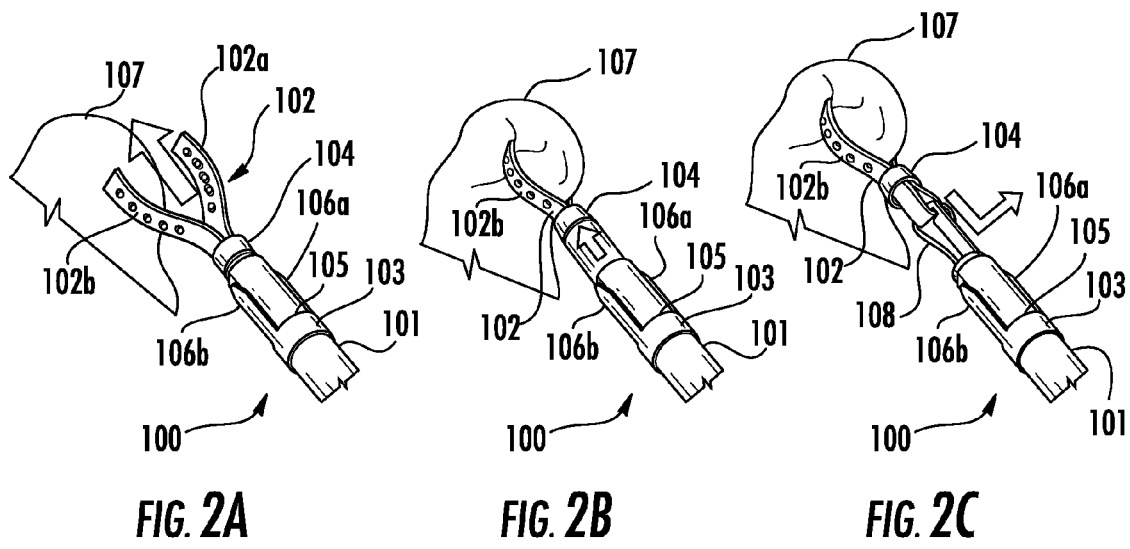
FIGS. 2A-C are perspective views of an exemplary tissue retractor at progressive stages of grasping a tissue or organ.

With reference to FIGS. 2A-C, the tissue retractor assembly 100 is depicted at progressive steps of grasping an organ or tissue 107 after the tissue refractor assembly 100 has been introduced into the port (not shown). With specific reference to FIG. 2A, the tissue retractor assembly 100 is depicted with the grasper 102, which had been loaded into the cannula 101 for purposes of introduction into the port, and the first leg 102a and second leg 102b have been extended out of a distal end of the cannula 101. Once inside the port, and at the organ 107 to be grasped, the grasper 102 is pushed out of the distal end of the cannula 101 by a hook (not shown) attached to the proximal end of the grasper 102. Generally, the clinician has a multipurpose 5 mm grasper in the surgical field during the procedure for managing the tissue of the organ in question. As depicted in FIG. 2A, the first leg 102a and the second leg 102b of the grasper 102 have been extended from the distal end of the cannula 101 and are used to surround the organ 107 to be grasped.

With reference to FIG. 2B, the grasper 102 has been positioned sufficiently around the organ 107 to be grasped and the locking ring 104 is utilized to lock the grasper 102 around the organ 107. Specifically, the locking ring 104 is pushed distally by the interior cannula (not shown) while the interior hook holds the grasper 102 in position. Thus, the locking mechanism 104 clenches the first leg 102a and second leg 102b around the organ 107.

With reference to FIG. 2C, once the grasper 102 is locked, the cannula 101 is retracted and lifted to release the hook, wherein the hook is pushed distal allowing the grasper 102 to be deployed from the cannula 101. As depicted in FIG. 2C, the tissue retractor assembly 100 further includes a suture 108 which secures and allows adjustment of the grasper 102 relative to the anchor 103. Specifically, the suture 108 is attached to the apex of the first and second legs, 102a and 102b, respectively, and the cannula 101 trails the suture form the distal tip.

Figure 3:
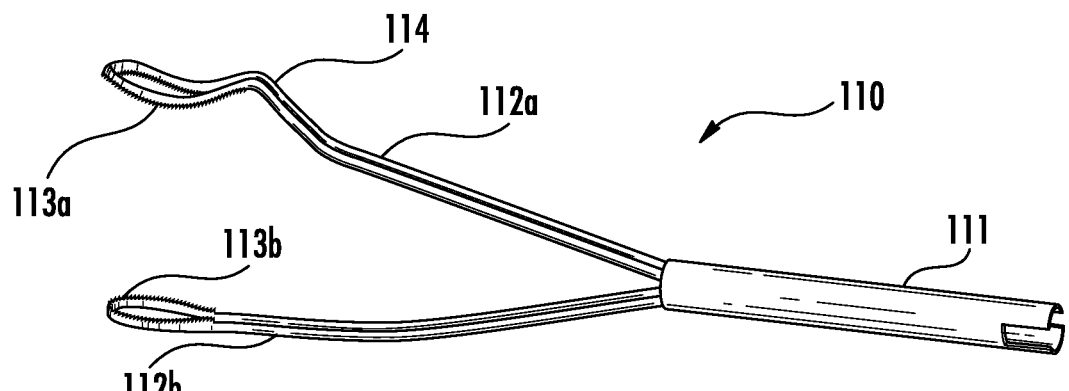
FIG. 3 is a perspective view of an exemplary grasper in an open position.

Turning now to FIGS. 3-6, another embodiment of the invention is shown as grasper 110, and provides a sufficiently wide opening for gripping an organ or tissue. With reference to FIG. 3, the grasper 110 is depicted in an "open" position and includes a first leg 112a and second leg 112b and a locking sleeve 111. The first and second leg 112a and 112b may be made of stainless wire and may be formed into shape. Distal ends 113a and 113b are preferably each formed as a loop so as to provide a more spread out and thus more stable area with which to grasp tissue or an organ. Additionally, one of the at least first and second leg 112a and 112b may have surface features, i.e., serrations, on a distal end of the first leg 113a and/or a distal end of the second leg 113b. The first leg 112a additionally may include an angled area 114 between the distal end of the first leg 113a and the distal end of the locking sleeve 111. Specifically, the angled area 114 includes angled bends up and down relative to the surface of the first leg 112a, wherein the angled bends may be approximately 45°, to thereby enable the adequate opening of the grasper. Further with reference to FIG. 3, instead of a locking ring as described above in connection with FIG. 2, a locking sleeve 111 is depicted, which is preferably configured as an elongated tube to provide stronger locking force, to slide more readily without getting cocked askew of the sliding axis, and to provide better ergonomics for the user at the proximal end.

Figure 4:
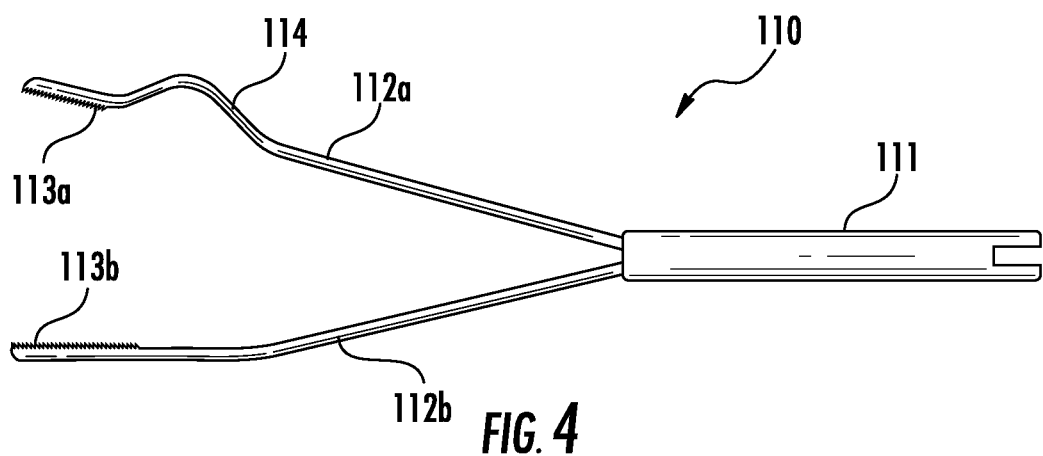
FIG. 4 is a side view of an exemplary grasper in an open position.

With reference to FIG. 4, an additional side view of the preferred grasper 110 in an "open" position is depicted for providing a clearer view of the angled area 114. The second leg 112b may be either formed in a straight manner or may contain a curve in order to provide a stronger or more secure grip on the organ or tissue when the first leg 112a and second leg 112b are clinched shut.

Figure 5:
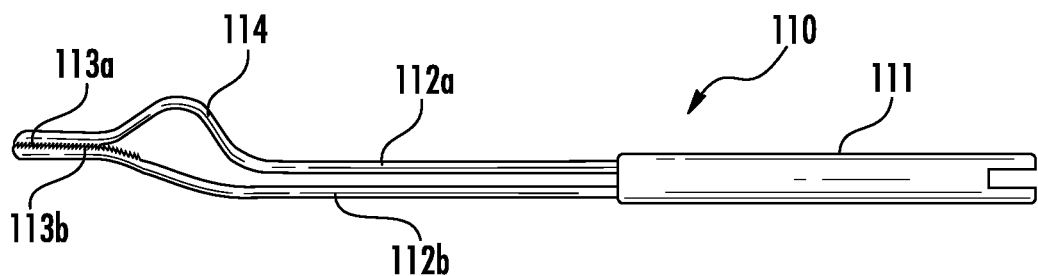
FIG. 5 is a side view of an exemplary grasper in an initial closed position.

With reference to FIG. 5, the grasper 110 is depicted in a "closed" position. As the locking sleeve 111 is pushed distally by the cannula 101 in the direction of the distal end of the first and second leg, 113a and 113b, respectively, the first leg 112a and second leg 112b clinch shut.

Figure 6:
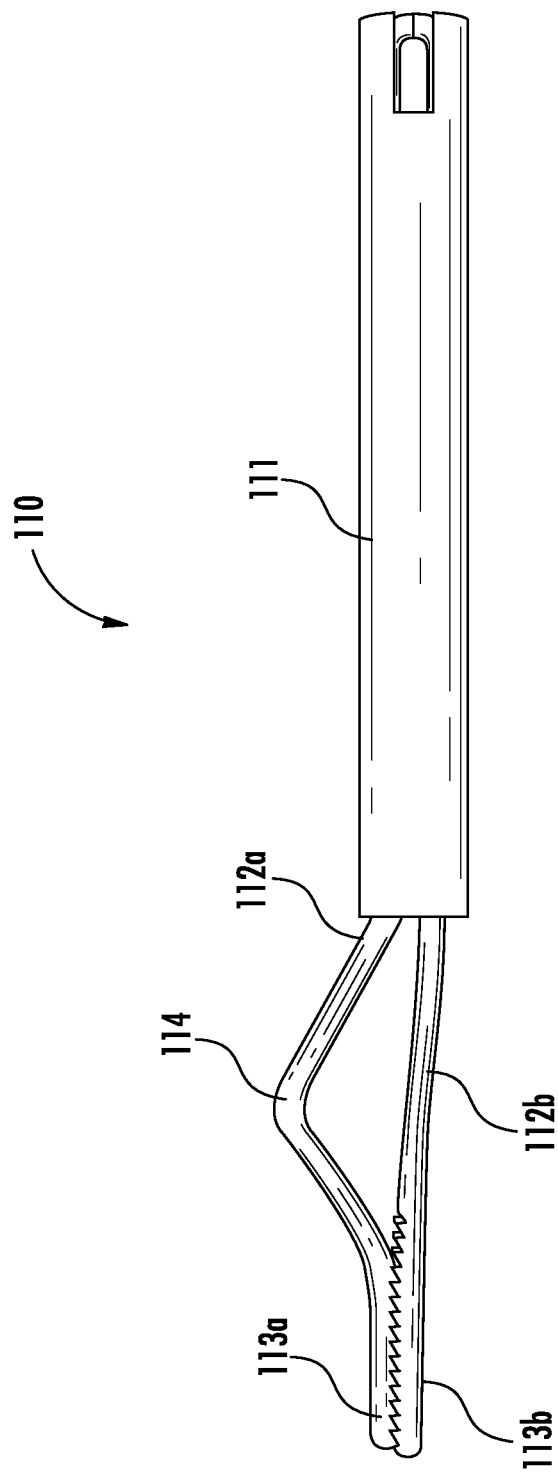
FIG. 6 is a side view of an exemplary grasper in a final closed position.

With reference to FIG. 6, the grasper 110 is depicted in a "closed" position where the locking sleeve 111 has been pushed distally by the cannula 101 to the furthest possible point. It would be understood by those with ordinary skill in the art that as the locking sleeve 111 is pushed closed to the distal end of the first and second leg, 113a and 113b, respectively, the first leg 112a and second leg 112b would be pushed together with an increasing force, thereby providing the clinician a range of forces which may be applied by the grasper 110 in order to sufficiently grip the organ or tissue.

Figure 7:
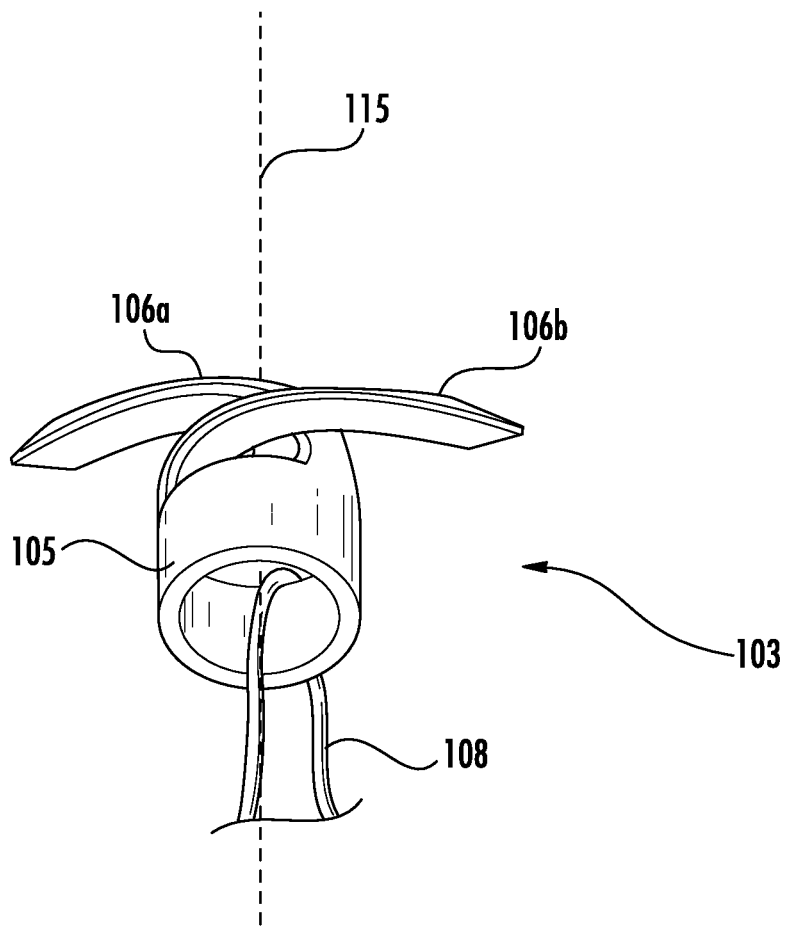
FIG. 7 is a perspective view of an exemplary anchor in a released position.

Turning now to FIG. 7, an exemplary embodiment of the anchor 103 is depicted. The tissue retractor assembly 100 is used to deploy the anchor 103 to an abdominal wall. The anchor 103 may be fabricated from a preformed shape memory nitinol staple which could be formed from a single wire form or cut from a tube. The fundamental structure of the anchor 103 is a cylindrical body 105 attached to at least two sharpened thin legs 106a and 106b that lie along an axis 115 of the cylindrical body 105. The at least two sharpened thin legs 106a and 106b are sharpened to allow them to penetrate tissue. The preformed nature of the at least two sharpened thin legs 106a and 106b allows the at least two sharpened thin legs 106a and 106b to return to their preformed shape in order to increase the pull out force of the anchor. As depicted in FIG. 1, the anchor 103 is initially loaded over a "D" or specifically shaped cannula 101 that helps to constrain the at least two sharpened thin legs 106a and 106b and allows the anchor 103 to be deployed by a simple tube over a tube push mechanism. With reference to FIG. 7, the anchor 103 is depicted in a "released" position, wherein the at least two sharpened thin legs 106a and 106b were preformed to fold in towards the axis 115 and center of the cylindrical body 106.

Figure 8:
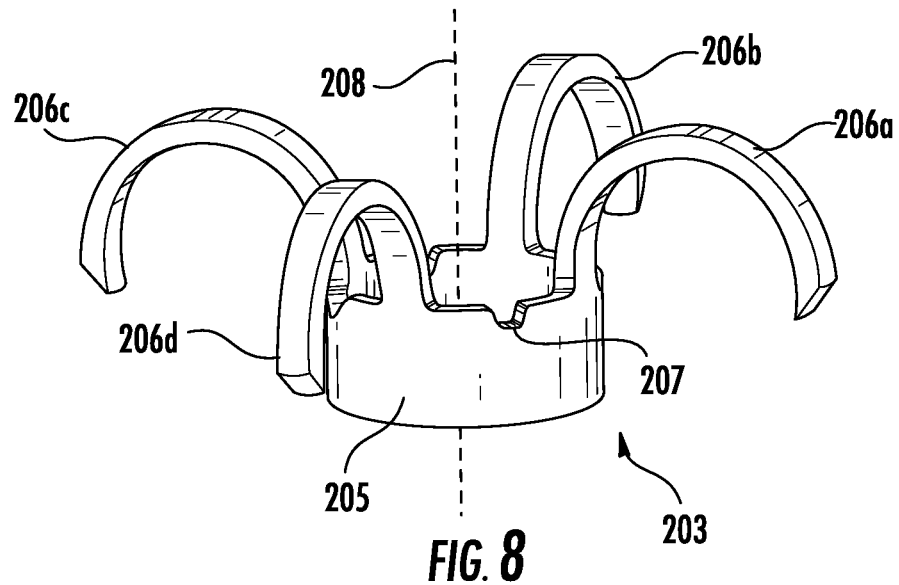
FIG. 8 is a perspective view of an exemplary anchor with a different configuration in a released position.

With reference to FIG. 8, an embodiment of the anchor 203 of the invention is depicted. Unlike the anchor 103 in FIG. 7, the anchor 203 in FIG. 8 includes the at least two (preferably four) sharpened thin legs 206a, 206b, 206c and 206d preformed to curve outwardly from the axis 208 and the center of the cylindrical body 205. As in FIG. 7, the anchor 203 of FIG. 8 also has cylindrical body 205 as the fundamental structure of the anchor 203, and the cylindrical body 205 is attached to or formed integrally with the at least two sharpened thin legs 206a, 206b, 206c and 206d. The anchor 203 may also include grooves or notches 207 in the cylindrical body 205 for purposes of guiding the suture 108, as is further discussed with relation with FIG. 9.

Figure 9:
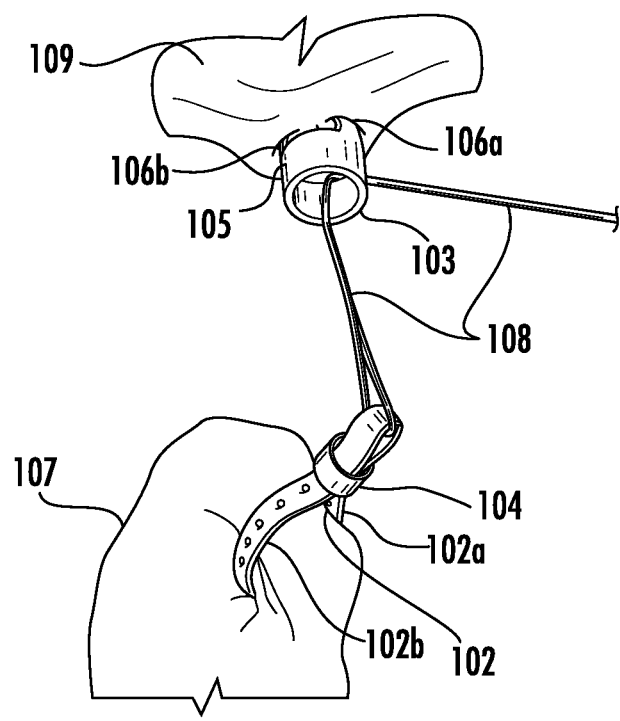
FIG. 9 is a perspective view of an exemplary grasper and anchor in operation.

With reference to FIG. 9, anchor 103 or 203 is attached by positioning the distal tip of the cannula 101 on the abdominal wall 109, the clinician's hand usually palpates on the outside of the abdominal wall 109, and the cannula 101 pushes the anchor 103 or 203 axially distal off of the cannula 101 as the anchor 103 or 203 penetrates the tissue 109. As the anchor 103 or 203 is released from the cannula 101, the at least two sharpened thin legs 106a and 106b or 206a, 206b, 206c and 206c curve in or away from the center of the cylindrical body 105 or 205 and thus provide a sufficient pull out force as well as protect the clinician from injury.

FIG. 9 further depicts the exemplary grasper 102 and anchor 103 in operation. Specifically, the grasper 102 has clinched the organ 107 and has been locked in position by the locking mechanism 104. Additionally, the anchor 103 has been released from the cannula 101 and the preformed at least two sharpened thin legs 106a and 106b have returned to their preformed shape in order to provide a sufficient pull out force. It should be noted that the grasper 102 is movably secured to the anchor 103 by the suture 108. The cannula 101 is retracted from the port trailing the suture 108 which keeps all the components tethered and allows the clinician to retract the organ 107 by increasing the tension on the suture 108. The suture 108 can be secured outside the port with a clamp or other appropriate means. At the end of the surgery, the grasper 102 will be removed with the organ 107 (in the case of a gall bladder removal or similar "-ectomy" surgery). The anchor 103 can be removed by gripping it with a 5 mm grasper (not shown) and pulling along the axis of the anchor 103 to remove it from the abdominal wall. Both parts of the tissue refractor assembly 100 can be removed through the abdominal incision created by the introduction of the port. The operation of the preferred grasper 110 of FIGS. 3-6 is substantially similar to the above description of the operation in connection with FIG. 9.

Figure 10:
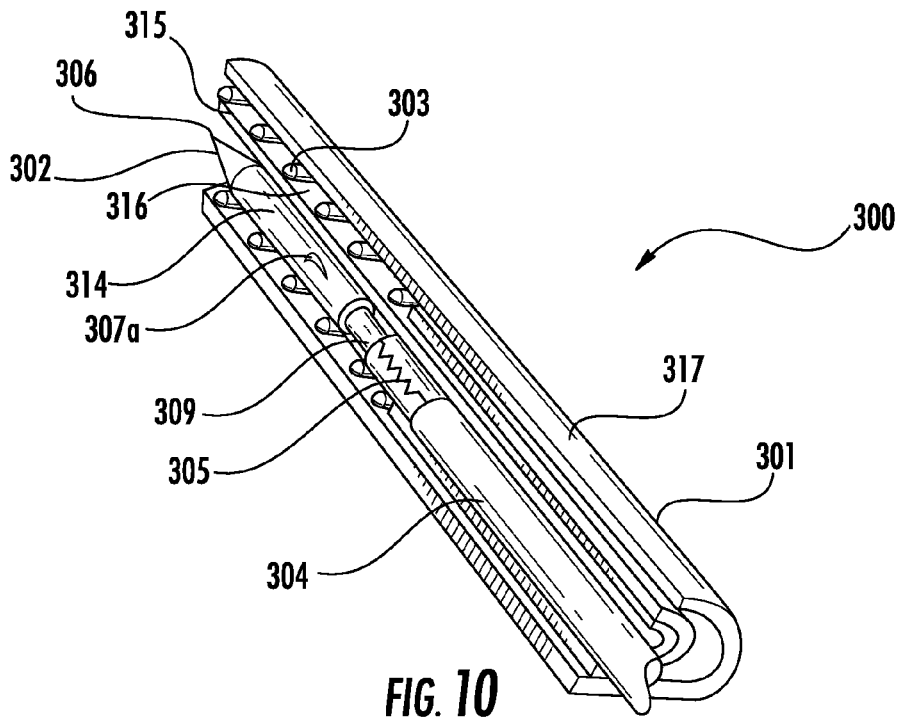
FIG. 10 is a perspective view of an exemplary tissue retractor cannula housing an anchor, a wire form and a grasper.

Now turning to FIG. 10, an alternate tissue refractor assembly 300 is depicted in accordance with the present disclosure. In the exemplary embodiment of FIG. 10, the tissue retractor assembly 300 includes a cannula 301 which houses an anchor 302, a wire form 303 and a grasper 304. The anchor 302 is configured and dimensioned to be deployed from the cannula 301 and attached to an abdominal wall anterior to an organ. The anchor 302 includes an outer tube 314 and a central shaft 309, the central shaft 309 further including at least two barbs 308a and 308b, depicted in FIG. 11B, which are configured to be deployed from the outer tube 314 when the central shaft 309 is axially pulled. Additionally, the anchor 302 includes a retractable sharp tip 306 which retracts into the outer tube 314 when the central shaft 309 is pulled axially to deploy the at least two barbs 308a and 308b. The wire form 303 may be fabricated as a coiled spring configured and dimensioned to deploy out of a distal end of the cannula 301 and expand radially. Further, the wire form 303 is secured and adjusted relative to the anchor 302 by a length of suture 311. Lastly, the grasper 304 is configured and dimensioned to extend out of the distal end of the cannula 301 and through the wire form 303, grasp tissue 313 (depicted in FIG. 13), and retract into the distal end of the cannula 301 to pull tissue 313 into the wire form 303. The grasper 304 may be a pediatric-type grasper with specialized jaws 305.

Still with reference to FIG. 10, the tissue refractor assembly 300 is based upon a 5 mm cannula 301 commonly used in the design of laparoscopic surgical tools. The cannula 301 contains both the anchor 302 and the wire form 303 used to grasp the organ or tissue 313. The components of the cannula 301 are arranged coaxially with the anchor 302 in the center with a fully functional 3 mm grasper 304 proximal to the anchor 302. Separated by a cannula wall 315, the wire form 303 is compressed into an annular ring 316 surrounded by the outer cannula wall 317.

The anchor 302 is constructed in two pieces, the outer tube 314 which forms the body of the anchor 302 and internal to the outer tube 314, the central shaft 309 which includes the retractable sharp tip 306 and at least two barbs 308a and 308b integrated that can be deployed by pulling the central shaft 309 of the anchor 302 proximal to the retractable sharp tip 306. The anchor 302 may be fabricated from metal or plastic.

Figure 11A:
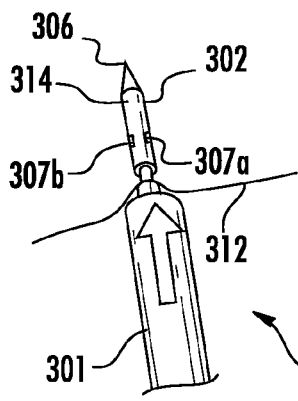
FIGS. 11A-C are perspective views of an exemplary tissue retractor at progressive stages of deploying an anchor.
Figure 11B:
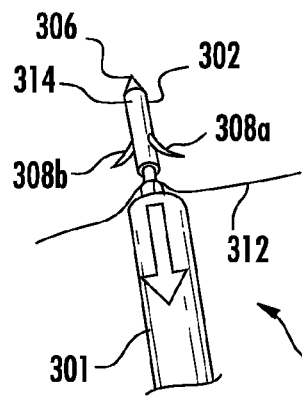
Figure 11C:
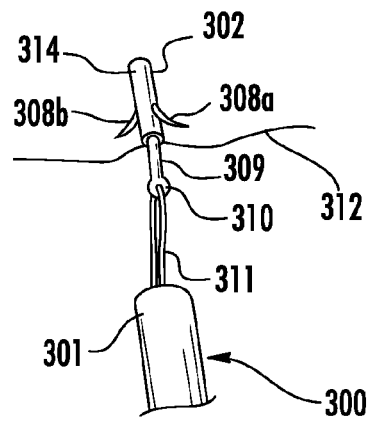

With reference to FIGS. 11A-C, the tissue retractor assembly 300 is depicted at progressive steps of securing the anchor 302 to the abdominal wall 312 after the tissue retractor assembly 300 has been introduced into the SILS port (not shown). Initially, the distal tip of the cannula 301 is positioned on the abdominal wall 312. The clinician's hand usually palpates on the outside of the abdominal wall 312. A specially designed 3 mm grasper 304, commonly used in pediatric laparoscopic procedures, is utilized to push the anchor 302 axially distal to penetrate the tissue 312. The 3 mm grasper 304 then retracts in order to retract the sharp tip 306 and deploy the at least two barbs 308a and 308b, as depicted in FIGS. 11A and 11B. Specifically, the at least two barbs 308a and 308b deploy through openings 307a and 307b in the outer tube 314 of the anchor 302. The at least two barbs 308a and 308b dramatically increase the holding force of the anchor 302 in the abdominal wall 312. As depicted in FIG. 11C, the anchor 302 further has a suture 311 attached to the proximal end and the cannula 301 trails the suture 311 from the distal tip. The suture 311 may be attached to the proximal end of the central shaft 309 of the anchor 302 by a ring 310 or similarly shaped component.

Figures 12A, 12B, 12C, 12D, 12E:
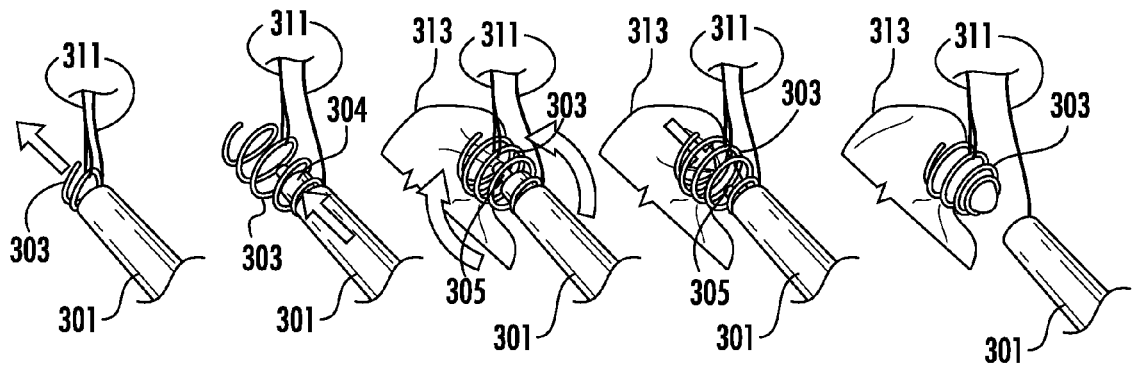
FIGS. 12A-E are perspective views of an exemplary tissue retractor at progressive stages of deploying a wire form.

With reference to FIGS. 12A-E, the tissue retractor assembly 300 is depicted at progressive steps of grasping an organ 313 after the tissue retractor assembly 300 has been introduced into the port and the anchor 302 has secured to the abdominal wall 312. Generally, a clinician has a multipurpose use 5 mm grasper (not shown) in the surgical field during the procedure. The 5 mm grasper manages the tissue of the organ in question during the grasping of the organ. The wire form 303 is in essence a specifically designed coiled spring which may have features such as surface roughness or barbs along the interior wire surface to enhance the gripping of the organ 313. As depicted in FIG. 12A, the wire form 303 is pushed out of the distal end of the cannula 301 and expands radially to enable a larger diameter profile which can accommodate more tissue of the organ 313. The 3 mm grasper 304 is then extended from the distal end of the cannula 301 to reach through the wire form 303, grasp the organ 313 and retract back into the distal end of the cannula 301 to pull tissue of the organ 313 into the wire form 303, which will grip the organ 313 by virtue of the forces generated between the surfaces of the wire form 303 and organ 313. With reference to FIG. 12E, once the wire form 313 has been secured around the organ 313, the wire form 303 is secured and adjusted relative to the anchor 302 by a length of suture 311. Specifically, the length of suture 311 is attached to the wire form 303, extends to the ring 310 of the anchor 302, as depicted in FIG. 11C, and is attached to the cannula 301.

Figure 13:
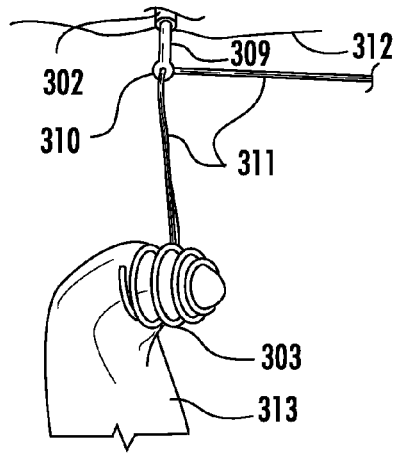
FIG. 13 is a perspective view of an exemplary anchor and wire form in operation.

With reference to FIG. 13, the exemplary wire form 303 and anchor 302 are depicted in operation. Once the wire form 303 and anchor 302 are attached to the organ 313 and abdominal wall 312, respectively, the cannula 301 is retracted from the port trailing the length of suture 311, which keeps all the components tethered and allows the clinician to retract the organ 313 by increasing the tension on the length of suture 311. The length of suture 311 can be secured outside the port with a clamp or other appropriate means (not shown). At the end of the surgery, the grasper 303 will be removed with the organ 313 (in the case of a gall bladder removal). Removal of the anchor 302 will require the reintroduction of the cannula 301, which contains the 3 mm grasper 304. A 5 mm grasper could be used to grip the outer tube 314 of the anchor 302, while the 3 mm grasper 304 is used to attach to the central shaft 309 of the anchor 302 and push distally to retract the at least two barbs 308a and 308b to allow the anchor 302 to be removed from the abdominal wall 312. The anchor 302 could be retracted into the cannula 302 or removed through the 5 mm port individually. Both components of the cannula 301 may also be removed through an abdominal incision created by the introduction of the port as both are tethered to the length of suture 311.

Figure 14:
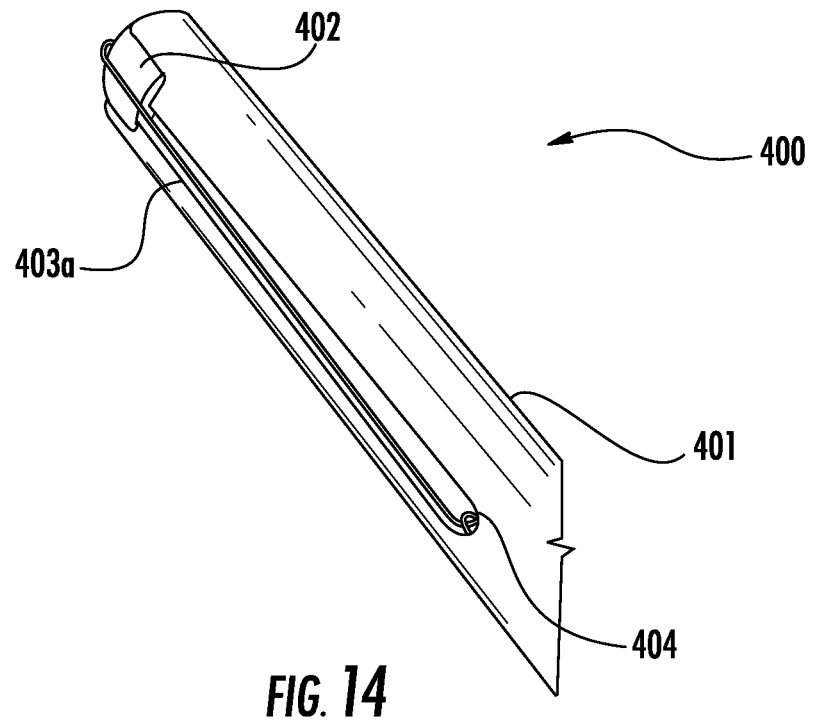
FIG. 14 is a perspective view of an exemplary tissue retractor cannula housing an anchor and a grasper.
Figure 15:
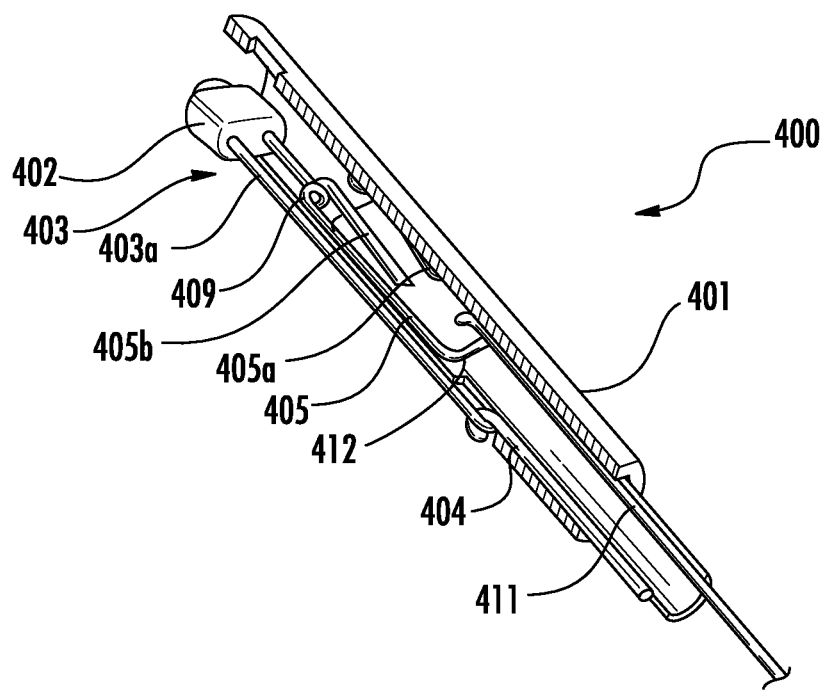
FIG. 15 is a partial section view of an exemplary tissue retractor cannula housing an anchor and a grasper.
Figure 16A:
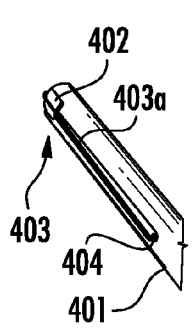
FIGS. 16A-D are perspective views of an exemplary tissue retractor at progressive stages of grasping an organ or tissue.
Figure 16B:
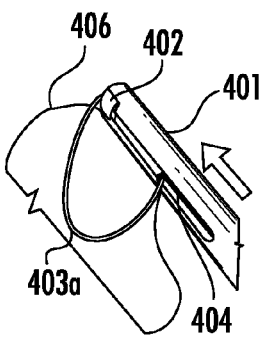
Figure 16C:
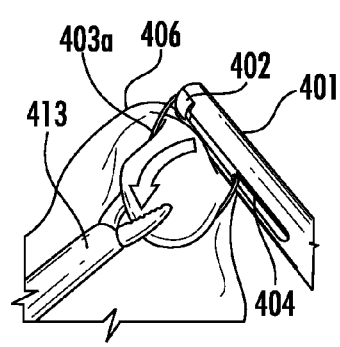
Figure 16D:
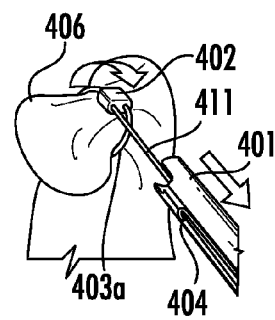
Figure 17A:
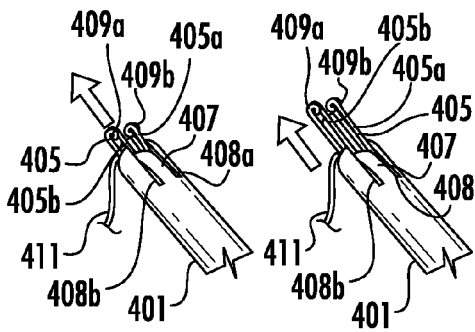
FIG. 17A-D are perspective views of an exemplary tissue retractor at progressive stages of deploying an anchor.
Figure 17B:
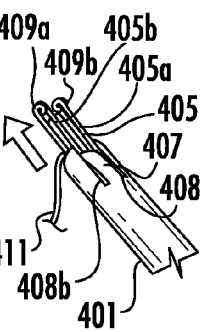
Figure 17C:
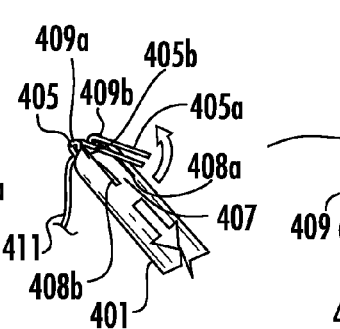
Figure 17D:
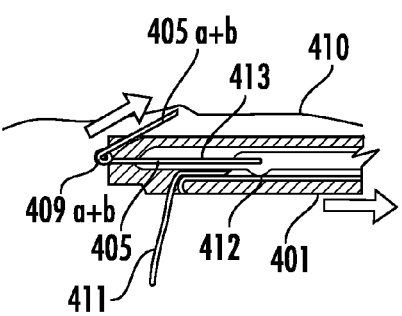

Now turning to FIGS. 14 and 15, an alternate tissue retractor assembly 400 is depicted in accordance with the present disclosure. FIG. 15 provides a partial view of the alternate tissue retractor assembly 400 for a more convenient depiction of the internal components of the tissue retractor assembly 400. In the exemplary embodiment of FIGS. 14 and 15, the tissue retractor assembly 400 includes a cannula 401, which houses an anchor 405 and a grasper 403. The grasper 403 is comprised of a loop of suture 403a with a one way locking toggle 402, configured and dimensioned to be released distally from the cannula 401. Specifically, the loop of suture 403a is configured and dimensioned to grasp tissue of an organ 406, retract into the distal end of the cannula 401 and tighten around the tissue of the organ 406. The anchor 405 includes a back span 412, torsion springs 409 and an axial connection between the back span 412 and torsion springs 409. The anchor 405 further includes two sharpened legs 405a and 405b configured and dimensioned to deploy from a distal end of the cannula 401. The grasper 403 is secured and adjusted relative to the anchor 405 by a length of suture 411.

Further with reference to FIGS. 14 and 15, the tissue retractor assembly 400 is based upon a 5 mm cannula 401 commonly used in the design of laparoscopic surgical tools. The cannula 401 contains both the grasper 403 to attach to an organ 406 and an anchor 405, as well as a system to deploy each. The components of the cannula 401 are arranged with both the grasper 403 and anchor 405 along the axis of the cannula 401 with the grasper 403 below the anchor 405, which may be fabricated as a spring clip. The cannula 401 may further include a slot to allow the deployment of the loop of suture 403a. The cannula 401 further includes features to aid in the delivery and firing or deployment of the grasper 403 and anchor 405.

With reference to FIGS. 16A-D, the tissue refractor assembly 400 is depicted at progressive steps of grasping an organ 406 after the tissue retractor assembly 400 has been introduced into the port (not shown). The grasper 403 is a suture based organ grasper including a loop of suture 403a with a one way locking toggle 402. The one way locking toggle 402 may be fabricated as a small molded plastic part which allows the loop of suture 403a to be pulled through in one direction, but stops the loop of suture 403a from loosening. The loop of suture 403a may also be a ribbon or similar structure to increase friction or distribute force more evenly. Additionally, the loop of suture 403a may have surface features, i.e., small cuts or barbs, on its diameter to increase the friction of the loop of suture 403a to the organ 406 and reduce the possibility of slipping. The loop of suture 403a is held flat in the cannula 401 by a hook 404 which is in the loop of suture 403a and holds tension on the loop of suture 403a in the cannula 401.

Still with reference to FIGS. 16A-D, in order to attach the loop of suture 403a to the organ 406, the cannula 401 would be introduced through the port and placed near the attachment site. The loop of suture 403a would be moved distal in order to produce slack in the loop of suture 403a. Generally, the clinician has a multipurpose use 5 mm grasper 413 in the surgical field during the procedure. The 5 mm grasper 413 manages the tissue of the organ 406 in question during the grasping of the organ 406. The 5 mm grasper 513 would be used to pull the tissue of the organ 406 through the loop of suture 403a. The delivery portion of the cannula 401 would pull the free end of the loop of suture 403a through the one way locking toggle 402 to tighten the loop of suture 403a around the tissue of the organ 406. By refracting the hook 404 and withdrawing the cannula 401, the one way locking toggle 402 and grasper 403 assembly could be released from the cannula 401. The free end of the loop of suture, a length of suture 411, would be trailed out of the distal end of the cannula 401 while approaching the attachment point for the anchor 405 to be attached to the abdominal wall 410.

With reference to FIGS. 17A-D, the tissue retractor assembly 400 is depicted at progressive steps of securing the anchor 405 to the abdominal wall 410 after the tissue retractor assembly 400 has been introduced into the port (not shown) and after the grasper 403 has been secured around the organ 406. The anchor 405 may be fabricated as a wire form constructed from a single piece of wire. The wire is a form which has a substantially symmetrical structure, consisting of a back span 412, torsion springs 409 and axial connections between the elements. The anchor 405 has a structure similar to the normally closed springs used in the typical construction of cloths pins. The anchor 405 further includes two sharpened legs 405a and 405b which are not connected by a cross member and are sharpened to facilitate tissue penetration. The anchor 405 is normally closed and resides in the cannula 401 in a tray 413, or similar structure, for deployment.

Still with reference to FIGS. 17A-D, the deployment of the anchor 405 requires that a device internal to the cannula 401 push the anchor 405 distal enough that the stripping feature 407 on the cannula 401 can wedge under the two sharpened legs 405a and 405b of the anchor 405. The tray 413 is then retracted proximally, which positions the two sharpened legs 405a and 405b of the anchor 405 to penetrate the abdominal wall 410. Specifically, the cannula 401 includes the stripping feature 407 and two slits 408a and 408b, which are dimensioned and configured to allow the two sharpened legs 405a and 405b of the anchor 405 to deploy from the distal end of the cannula 401 by an internal retracting mechanism when the anchor 405 has been partially deployed from the distal end of the cannula 401. Therefore, while the anchor 405 is normally closed in the tray 413, the two sharpened legs 405a and 405b can deploy from the cannula 401 through the two slits 408a and 408b in order to properly penetrate and attach to the abdominal wall 410.

Further with reference to FIGS. 17A-D, the distal tip of the cannula 401 is positioned adjacent to the abdominal wall 410. The clinicians hand usually palpates on the outside of the abdominal wall 410. The clinician would push the cannula 401 anterior, while pulling the cannula 401 and anchor 405 proximally. This would cause the two sharpened legs 405a and 405b of the anchor 405 to snag and penetrate the abdominal wall 410. The anchor 405 would then be released from the cannula 401 by retracting the cannula 401 and pushing the tray 413 distal. The closing action of the anchor 405 and the direction of the tension applied by the length of suture 411 would increase the holding force of the anchor 405.

Figure 18:
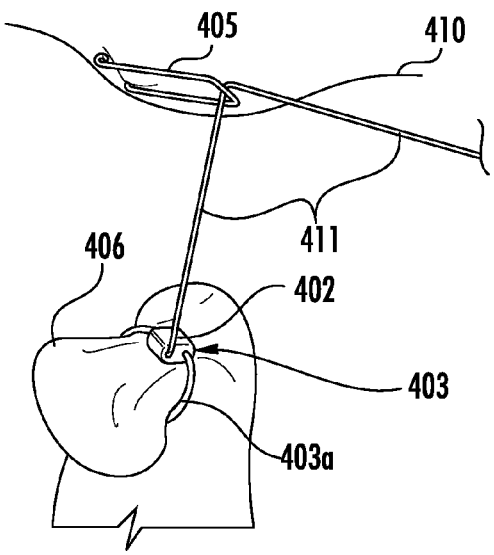
FIG. 18 is a perspective view of an exemplary anchor and grasper in operation.

With reference to FIG. 18, the exemplary anchor 405 and grasper 403 are depicted in operation. The cannula 401 is retracted from the port trailing the length of suture 311, which keeps all parts tethered and allows the clinician to retract the organ 406 by increasing the tension on the length of suture 411. The length of suture 411 can be secured outside the port with a clamp or other appropriate means. At the end of the surgery, the grasper 403 may be removed with the organ 406 (in the case of a gall bladder removal). The grasper 413, depicted in FIG. 16C, may further be used to grip the back span 412 of the anchor 405 and push away from the entry direction, thereby allowing the anchor 405 to be easily removed. The normally closed nature of the anchor 405 would render the two sharpened legs 405a and 405b safe in the abdominal cavity. Both the anchor 405 and grasper 403 of the tissue retractor assembly 400 may also be removed through the abdominal incision created by the introduction of the port as both are tethered to the suture.

Figure 19:
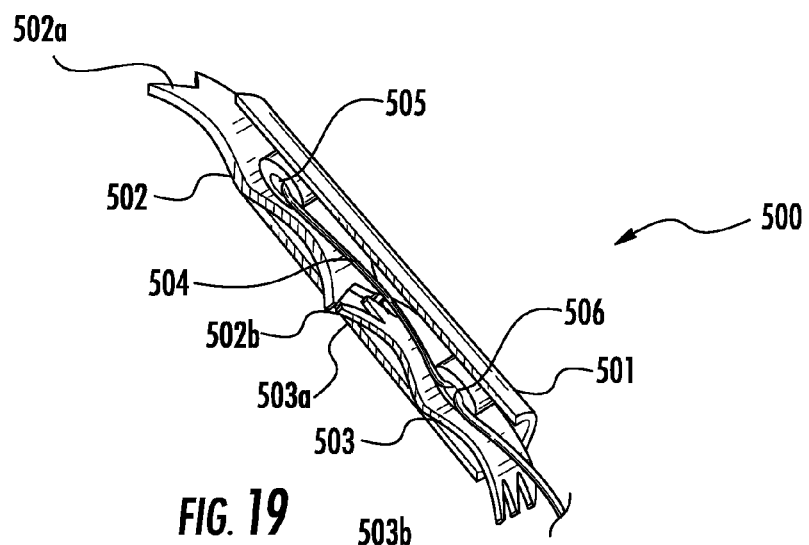
FIG. 19 is a partial section view of an exemplary tissue retractor cannula housing a first grasper and a second grasper.
Figures 20A, 20B, 20C, 20D, 20E:
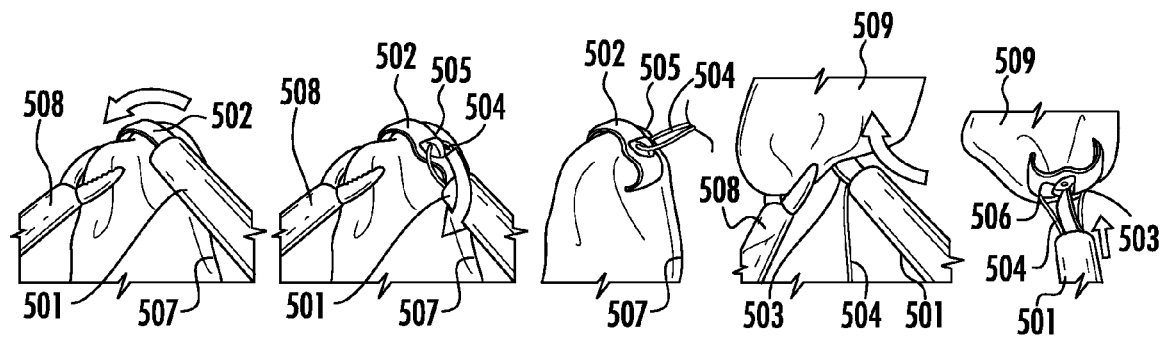
FIGS. 20A-E are perspective views of an exemplary tissue retractor at progressive stages of deploying the first grasper and second grasper.

Now turning to FIG. 19, an alternate tissue refractor assembly 500 is depicted in accordance with the present disclosure. In the exemplary embodiment of FIG. 19, the tissue retractor assembly 500 includes a cannula 501, which houses a first grasper 502 and second grasper 503. The first grasper 502 may be fabricated as a first clip configured and dimensioned to be deployed axially from a distal end of the cannula 501 and is defined by a C-shaped form after deployment from the cannula 501. The second grasper 503 may be fabricated as a second clip configured and dimensioned to be deployed axially from the distal end of the cannula 501 and is also defined by a C-shaped from after deployment from the cannula 501. The first grasper 502 is further secured and adjusted relative to the second grasper 503 by a length of suture 504, which is pre-threaded through the first and second grasper 502 and 503 and into the cannula 501.

The tissue retractor assembly 500 of FIG. 19 is based upon a 5 mm cannula 501 commonly used in the design of laparoscopic surgical tools. The cannula 501 deploys the first and second grasper 502 and 503, respectively, by pushing them sequentially out of the distal tip of the cannula 501. The first and second grasper 502 and 503 would be pushed forward by a rod or cannula 501 sliding axially and with a force supplied by a screw or gear driven mechanism (not shown). The first and second grasper 502 and 503 may be fabricated from metal, plastic or a combination of materials that are formed in either a "C" or "U" shape which is normally closed, i.e., Raney type clips. The first and second grasper 502 and 503 would have a first and second back span 505 and 506, respectively, for guiding or attaching a length of suture 504. The first and second grasper 502 and 503 may additionally have gripping features, i.e., teeth, points, chevrons, 502a, 502b, 503a and 503b, at the open tips or on the inside surface to aid in gripping tissue. The first and second grasper 502 and 503 for the organ 507 may further be coated with a rubber, have surface features or a shape that is advantageous to grasping without damaging the organ 507. Additionally, the second grasper 503, which is to be attached to the abdominal wall 509, may have more aggressive gripping features 503a and 503b, i.e., aggressive teeth or sharp points, to attach to the abdominal wall 509. The first grasper 502, however, which is to be used to grasp the organ 507, may have atraumatic teeth at the gripping features 502a and 502b, in order to prevent damage to the organ 507.

Still with reference to FIG. 19 and further with reference to FIGS. 20A-E, the tissue retractor assembly 500 is depicted at progressive steps of securing the first grasper 502 to the organ 507 and securing the second grasper 503 to the abdominal wall 509 after the tissue retractor assembly 500 has been introduced into the port (not shown). The first and second grasper 502 and 503, as they reside in the cannula 501, would be fully opened such that they are nearly flat. The first and second grasper 502 and 503 are loaded into the cannula 501 for purposes of introduction into the port. Once inside the port and at the organ 507 to be grasped, the first and second grasper 502 and 503 may be deployed. Generally, the clinician has a multipurpose use 5 mm grasper 508, depicted in FIG. 20A, in the surgical field during the procedure. The 5 mm grasper 508 manages the tissue of the organ 507 in question. The distal end of the cannula 501 is placed near the organ 507 and the first grasper 502 is pushed out of the cannula 501 distally by a rod or shaft which is driven by a screw or gear mechanism (not shown). The first grasper 502 will be pushed out approximately halfway to allow the clinician to position the first grasper 502 and then the first grasper 502 would be deployed. The shape of the cannula 501 and features at the tip would help to manage the dynamic nature of the first grasper 502 deployment. This design also offers the possibility of deploying multiple graspers onto the organ 507 as necessary (not shown). The cannula 501 trails a length of suture 504 that is tethered to the first grasper 502 placed on the organ 507.

Further with reference to FIGS. 20A-E, the second grasper 503 is deployed next to allow the organ 507 to be refracted. The second grasper 503 may have the same overall shape and function as the first grasper 502. The second grasper 503 may include more aggressive features on the gripping features 503a and 503b of the insufflated abdominal wall 509. The gripping features 503a and 503b may also be sharpened to the pint of forming penetrating features. The cannula 501 is advanced to the abdominal wall 509 and the general use 5 mm grasper 508 is used to manage the tissue of the abdominal wall 509. The second grasper 503 is deployed in a substantially similar method as the first grasper 502 attached to the organ 507.

Figure 21:
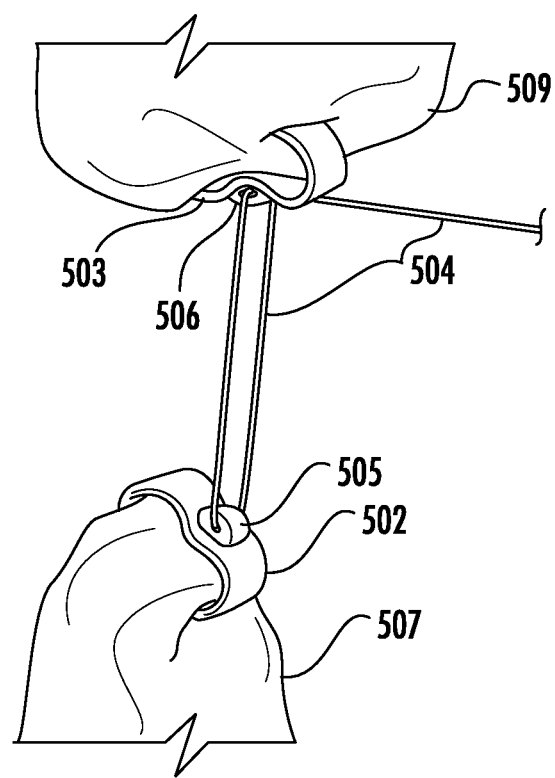
FIG. 21 is a perspective view of an exemplary first grasper and second grasper in operation.
Figure 22:
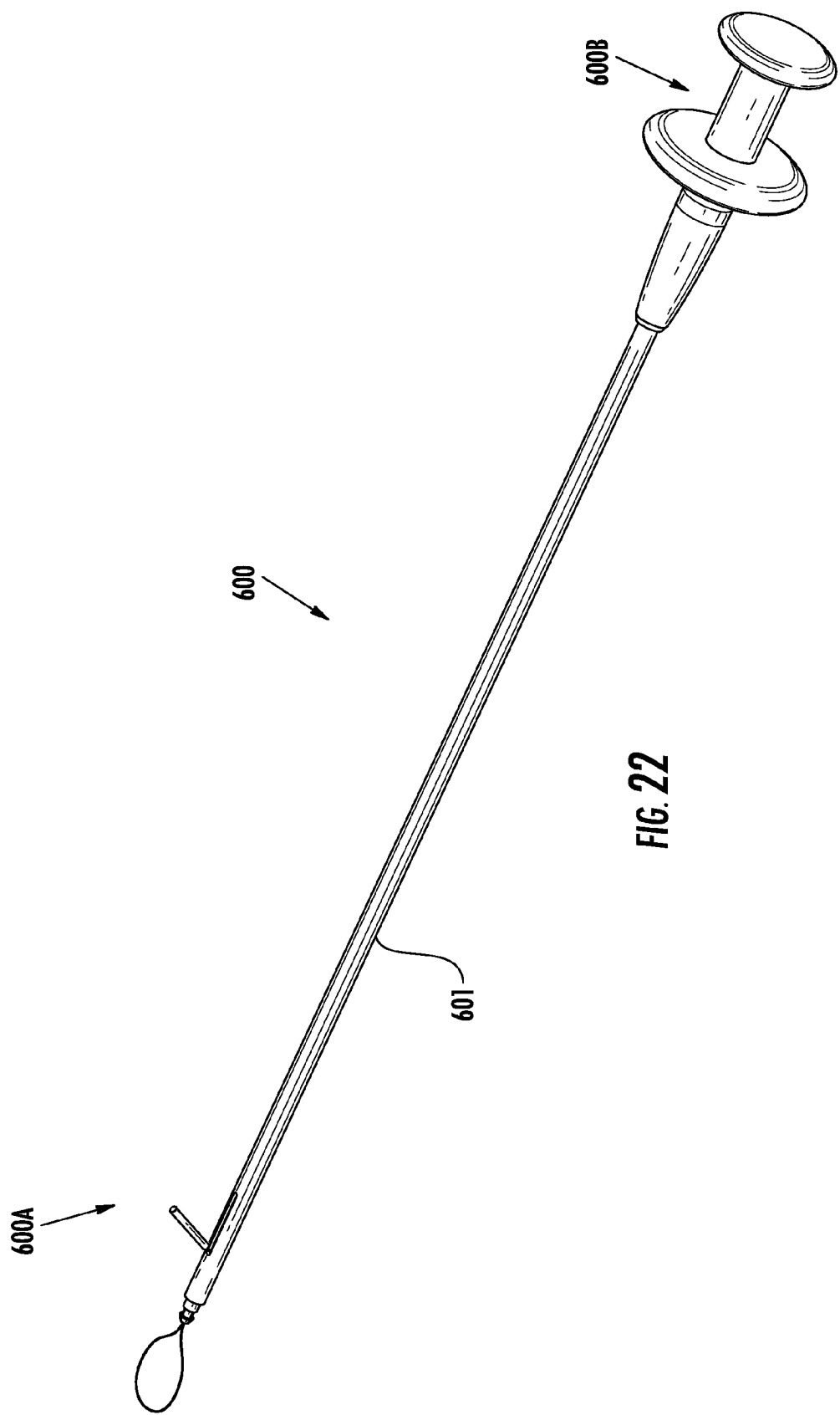
FIG. 22 is a perspective view of an exemplary anchor retrieval tool in accordance with the invention.

With reference to FIG. 21, the exemplary first grasper 502 and second grasper 503 are depicted in operation. The cannula 501 is retracted from the port trailing the length of suture 504 which keeps all the components tethered and allows the clinician to retract the organ 507 by increasing the tension on the length of suture 504. The length of suture 504 may be secured outside the port with a clamp or other appropriate means. At the end of the surgery, the first grasper 502 on the organ 507 may be removed with the organ 507 (in the case of a gall bladder removal). Depending on the geometry of the second grasper 503, removal of the second grasper 503 may require a specific tool which would be integrated into the cannula 501 or be a separate tool. If integrated into the cannula 501, the tool could be reintroduced to engage the second grasper 503 in order to remove it without damaging the tissue of the abdominal wall 509. Both the first and second grasper 502 and 503 may be removed through the abdominal incision created by the introduction of the port.

Once a surgical procedure utilizing the inventive assembly is completed, the assembly must be removed, at least in part. Although a biodegradable anchor (and thus not needing to be removed) is contemplated as being within the scope of the invention, the preferred embodiment of anchor 203 is made from a nondegradable material such as nitinol. As such, it is also preferred that the anchor be removed from the patient after the procedure is completed.

To this end, as depicted in FIGS. 22-26, the invention may also include anchor retrieval tool 600. Retrieval tool 600 is generally elongate in shape, having a distal end 600A and a proximal end 600B. Main body 601 is preferably substantially tubular in shape and adapted to fit through a surgical port.

Distal end 600A is shown in detail in FIG. 23. A locator loop 602 projects from the endmost portion of distal end 600A. Locator loop 602 is made from a wire, suture-type thread, or other flexible thin material, and it serves to enable easy location of the anchor in the body. Locator loop 602 is looped around the suture that is attached to anchor 203; the clinician can then guide the retrieval tool along the suture directly to anchor 203 where it is embedded in the abdominal wall, for example. One or both ends of loop 602 are attached to pull tab 604, which serves to tighten loop 602 as desired about the suture. As shown in FIG. 23, when pull tab 604 is pulled along main body 601 in the direction of arrow A, loop 602 is retracted within main body 601 and tightens in the direction of arrow B. The thus-tightened loop 602 is shown in dotted lines in FIG. 23. Other loop-tightening mechanisms (e.g., a lever) are contemplated as being within the scope of the invention.

Disposed within main body 601 is shaft 606 having a hollow bore 607 adapted to accommodate a suture (not shown). As best shown in FIGS. 23 and 24A, the distal-most end of shaft 606 includes a sloped portion 608 that terminates in a shoulder or flange 610 (to be discussed below). As best shown in FIG. 24B, the proximal end of shaft 606 passes through a handle portion 616 of main body 601 that includes a handle flange 620. A widened bore 618 is formed within handle portion 616 dimensioned to accommodate the wider proximal end 622 of shaft 606, which terminates in a pommel or handle 624. Floor 619 of bore 618 preferably acts as a stop mechanism to prevent hyper-insertion of the handle and thus overextension of the distal end of shaft 606 (which could injure the patient).

The above-described structure of the proximal and distal ends of shaft 606 enables the clinician to locate and remove an anchor from the patient's body upon conclusion of the surgery or procedure. For use of this exemplary retrieval tool 600, it is preferred to have used a slightly modified anchor 203' shown in FIG. 24A, for example. Anchor 203' is similar to anchor 203, having a cylindrical body 205' and four legs 206'. However, anchor 203' also includes at least one and preferably multiple flexible detent tabs 612 cut into cylindrical body 205'. Detent tabs 612 are angled inwardly towards the center of body 205'. When the distal end of shaft 606 enters the interior of anchor 203', sloping surface 608 pushes against tabs 612 as it slides past them, causing tabs 612 to flex outward. Then, as shown in FIGS. 25A-B, when the narrow neck 611 of shaft 606 is substantially adjacent tabs 612, tabs 612 snap back into their original position/configuration and catch underneath shoulder 610, thereby preventing removal of anchor 203' from the distal end of shaft 606. As shown in FIG. 26C, the clinician withdraws handle 624 in the direction of arrow C, and the distal end of shaft 606 pulls anchor 203' out of the tissue and downward into main body 601, and thence out of the patient.

A preferred embodiment of a tissue retractor assembly 700, including grasper 710, anchor 730, and universal user interface 740, is depicted in various views and stages of deployment in FIGS. 27-33.

Figure 28A:
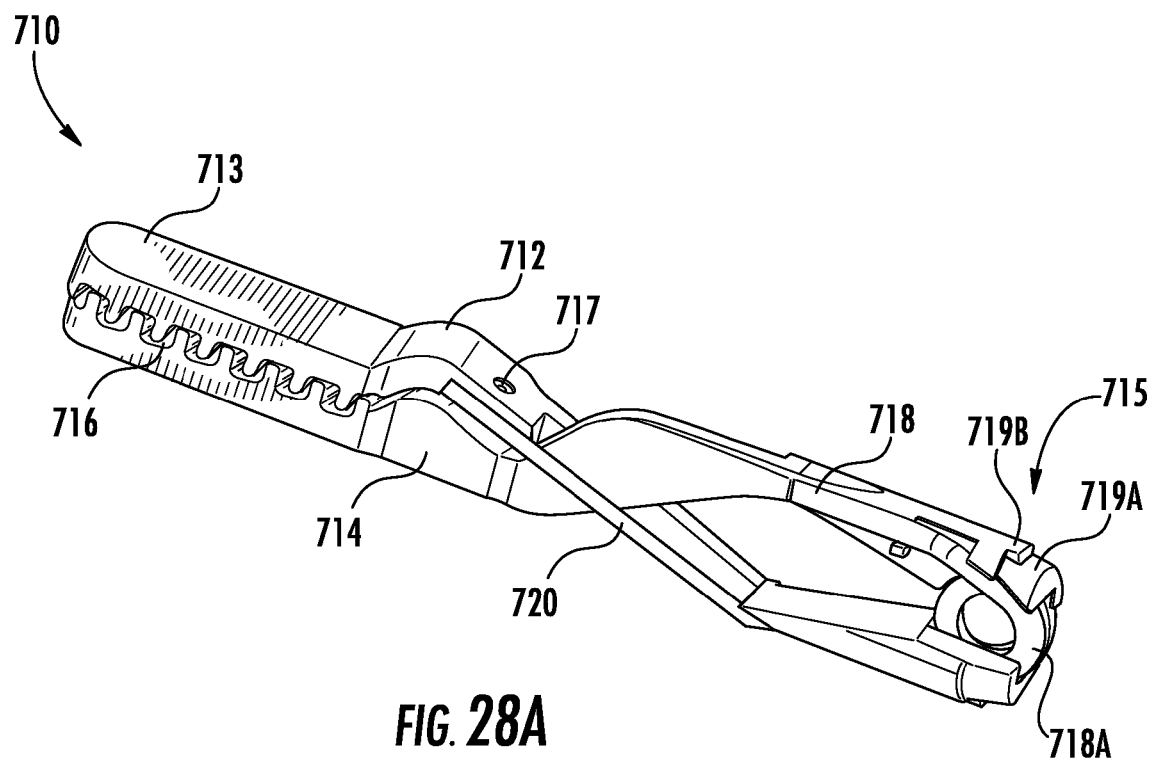
FIGS. 28A-B are perspective views of a tissue retractor grasper in accordance with the invention.
Figure 28B:
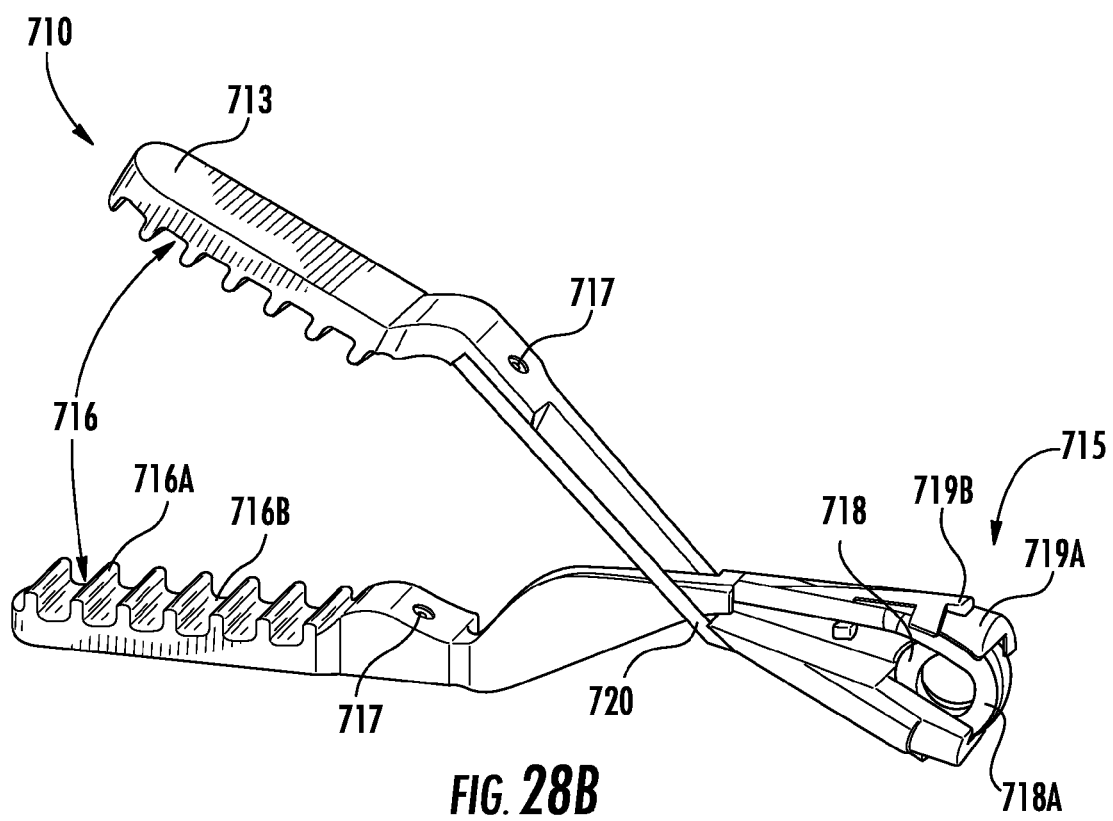

As shown in FIGS. 28-A-B, tissue grasper 710 is adapted to contact and secure the tissue or organ desired to be retracted. Grasper 710 includes opposable upper and lower arms 712 and 714, each having a distal end 713 and a proximal end 715. Interior facing surfaces of distal ends 713 form the actual tissue grasping jaws 716, typified by structure that creates a high coefficient of friction between grasper 710 and the tissue to be retracted. In the preferred embodiment, jaws 716 include undulating surfaces having peaks or teeth 716A and troughs 716B. The teeth 716A of one of arms 712 and 714 preferably matingly engage the troughs 716B of the other of arms 712 and 714 in an interleaved manner as shown in FIG. 28A. It is also preferred that jaws 716 be substantially smooth and free from sharp or jagged edges (i.e., teeth 716A are rounded) to avoid tearing or otherwise injuring the tissue to be retracted. Other embodiments of grasping surfaces are also contemplated.

Proximal ends 715 of arms 712, 714 are connected by coil spring 718 and wire strut 720. Spring 718 biases proximal ends 715 apart, thereby biasing distal ends 713 (and thus jaws 716) together and closed. In order to open jaws 716, force is applied to the proximal ends 715 of arms 712, 714, urging proximal ends 715 together. In one embodiment, this is accomplished by the relative withdrawal of grasper 710 into a tube or cannula 750 having an inner diameter or similar dimension smaller than the width of the proximal ends 715 when the grasper is in its FIG. 28A closed configuration. The relative withdrawal (i.e., either the grasper 710 is pulled within the tube 750 or the tube 750 is pushed over the grasper 710) of the grasper within the tube 710 causes the tube to cinch proximal ends 715 together, thereby opening jaws 716.

Figure 28D:
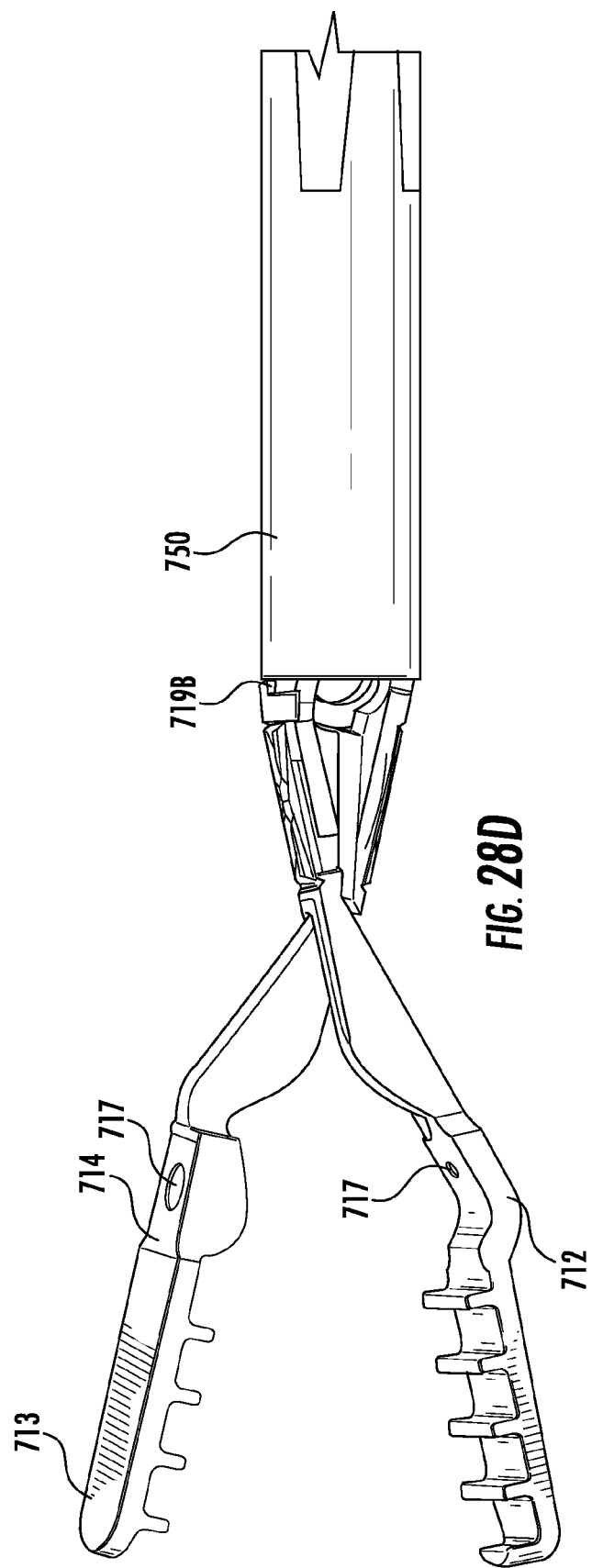

In a preferred embodiment of grasper 710, as shown in FIGS. 28-A-D, proximal ends 715 of arms 712, 714 are provided with a graduated diameter so that only a portion of the proximal end 715 resides and remains within the tube. In the preferred embodiment, proximal end 715 is provided at least in two stages: a narrower section 719A that fits within outer tube 750, and a wider boss section 719B that does not fit within the tube 750 (see FIG. 28C). When outer tube 750 is moved forward (or when the grasper is pulled backward), the distal rim or face of the tube pushes against bosses 719B so as to cause bosses 719B to pivot substantially around the axis of coil spring 718. Consequently, the proximal ends 715 of arms 712, 714 are pushed together, and distal ends 713 move apart, ready to grasp tissue in jaws 716, as shown in FIG. 28D.

When grasper 710 is secured onto tissue to be retracted, the user will pull on the suture there attached as described above in connection with the previous embodiments. This pulling, if done with enough force, could at least partially overcome the biasing force of coil spring 718 and loosen the grip of jaws 716 on the retracted tissue. So as to enhance the gripping force of the jaws, holes 717 are provided in both arms 712 and 714 distal to the pivot point of the arms. The suture (not shown) to which the grasper and anchor are attached is threaded through holes 717. As such, when the user pulls on the suture to retract the tissue secured within jaws 716, the pulling force on the suture is transmitted to arms 712 and 714 via holes 717 and tends to further close jaws 716, thereby securing the retracted tissue further. The harder the user pulls (within reason), the more "closing force" is transmitted to jaws 716 via the suture at holes 717.

Figure 29A:
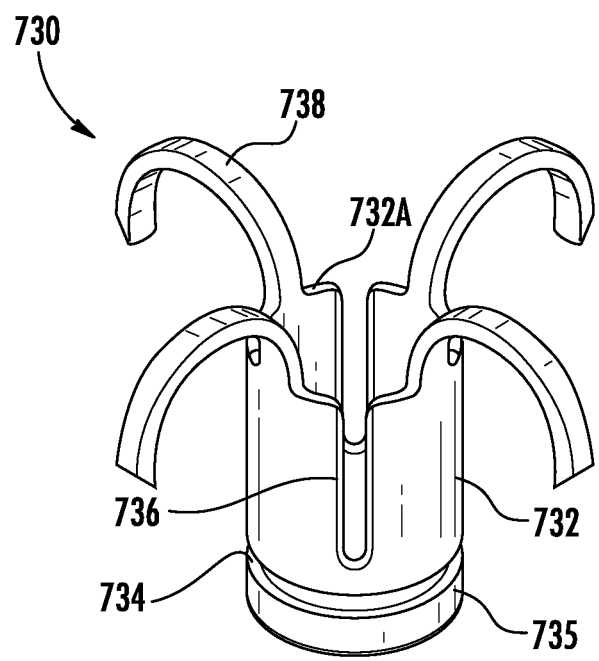
FIGS. 29A-B are perspective views of an anchor for intracorporeal tissue retraction in accordance with the invention.
Figure 29B:
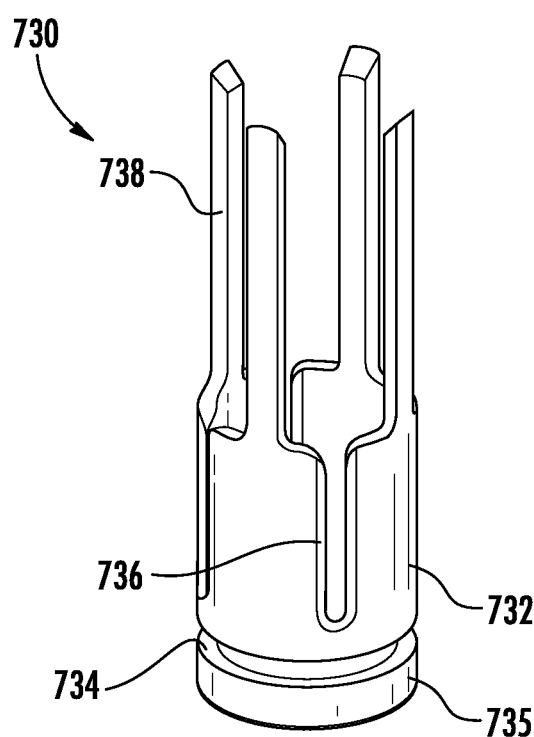

The preferred anchor 730 of tissue retractor assembly 700 is shown in FIGS. 29A-B. Anchor 730 includes main body 732 which has substantially at its proximal end a notched or necked down portion forming groove 734. In addition or alternatively, main body 732 can be substantially straight and provided with a proximal flange 735 that has a larger diameter than main body 732. In either event, an anchor securing mechanism (to be described below) latches onto either groove 734 or flange 735.

Main body 732 also includes at least one notch 736 formed preferably longitudinally therein. Notches 736 accommodate the suture or other movable support that is threaded through the anchor (and attached to grasper 710) so that the longitudinal movement of the suture does not abrade the abdominal wall tissue in contact with the distal edge 732A of main body 732 when anchor 730 is deployed. Additionally, notches 736 enable easier movement of the suture by the clinician since it will not be rubbing against the abdominal wall tissue nor be trapped between the abdominal wall tissue and distal edge 732A.

At the distal end of anchor 720 are provided a plurality of legs 738. Preferably, four such legs are provided. Anchor 730 is made from a resilient, preferably shape memory material such as nitinol. In its natural configuration, legs 738 are curved outwardly from main body 732 as shown in FIG. 29A. As shown in FIG. 29B, when anchor 730 is disposed within or withdrawn into a confining space such as outer tube 750, the tube uncurves legs 738 so that they are substantially straight as shown in FIG. 29B. That is, anchor 730 is in a "ready to be deployed" configuration as shown in FIG. 29B (i.e., inside outer tube 750) and is in a deployed configuration (i.e., secured in the abdominal wall) in FIG. 29A.

The nitinol or other shape memory material of anchor 730 can be selected to have different bending properties at different temperatures. In the preferred embodiment, a formulation or alloy is chosen that is more pliant at room temperature (approximately 20° C.) than at body temperature (approximately 37° C.). In such a case, legs 738 are more easily unbent from their straight, in-tube configuration when they are ready to be inserted into the abdominal wall. Then, after being disposed in the abdominal wall, the temperature of legs 738 rises to approximately body temperature, and legs 738 become less pliant. Thus, anchor 730 becomes more firmly deployed in the abdominal wall and less likely to be inadvertently or accidentally removed when removal is not desired.

Figure 27A:
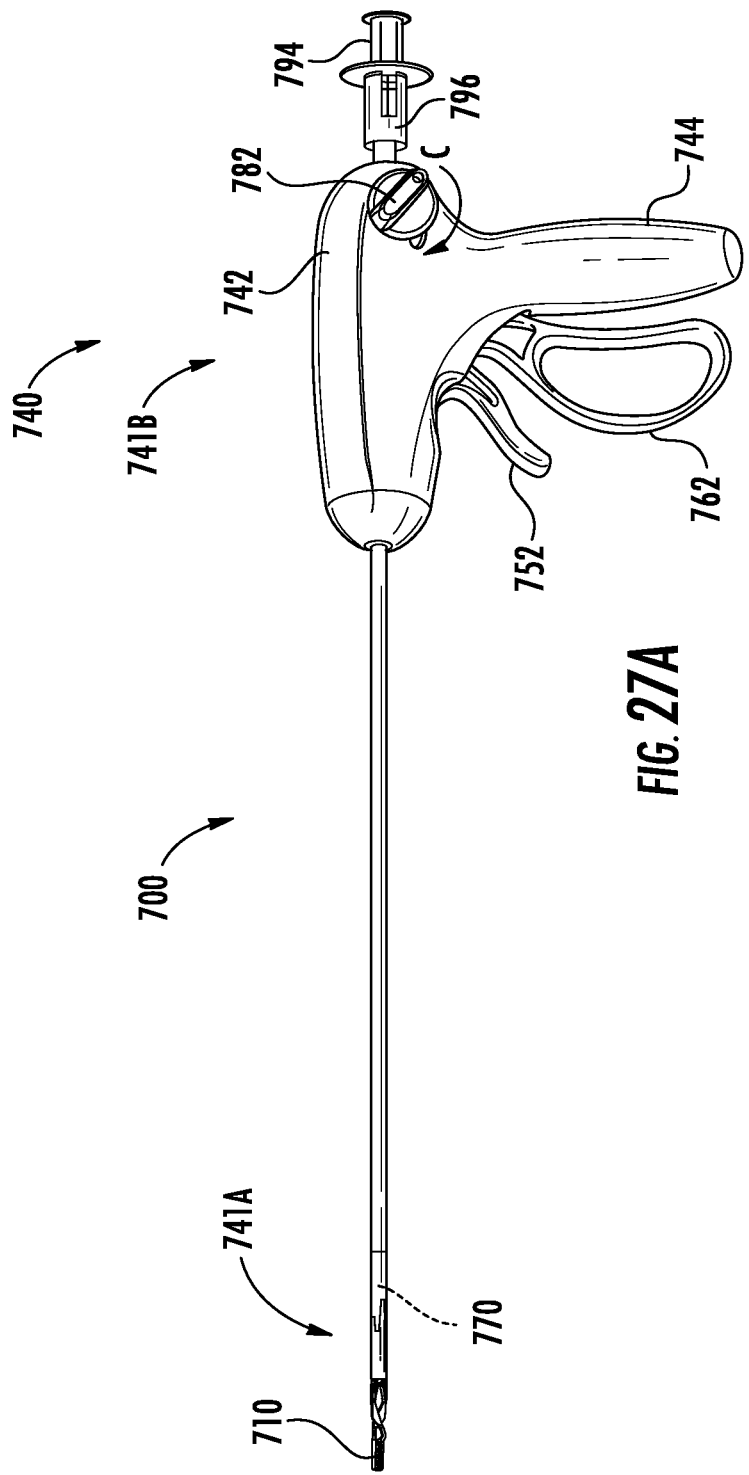
FIG. 27A is a perspective view of a tissue retractor assembly in accordance with the invention.
Figure 27B:
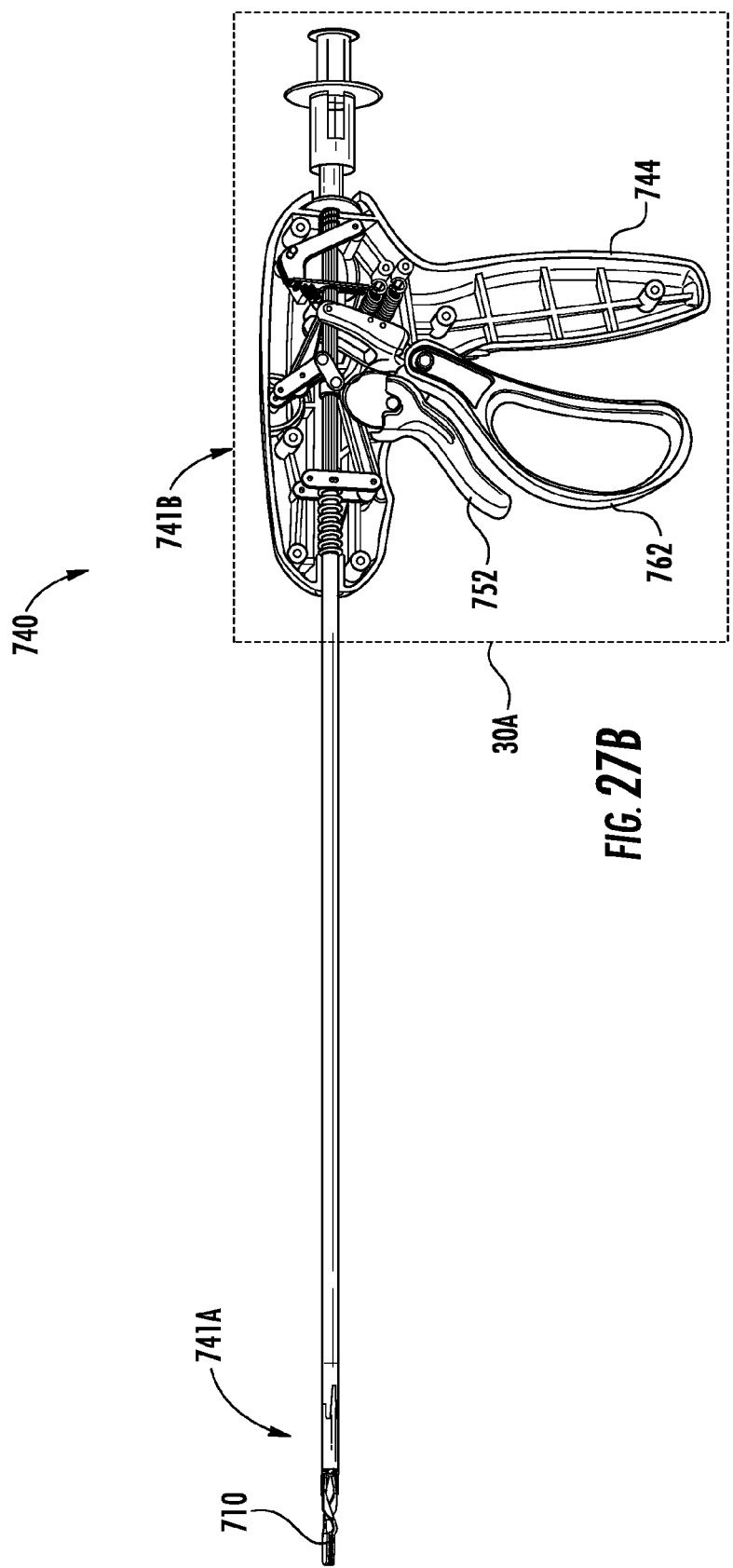
FIG. 27B is a perspective view of the tissue retractor assembly of FIG. 27A with the cover of the user interface removed for clarity.
Figure 30A:
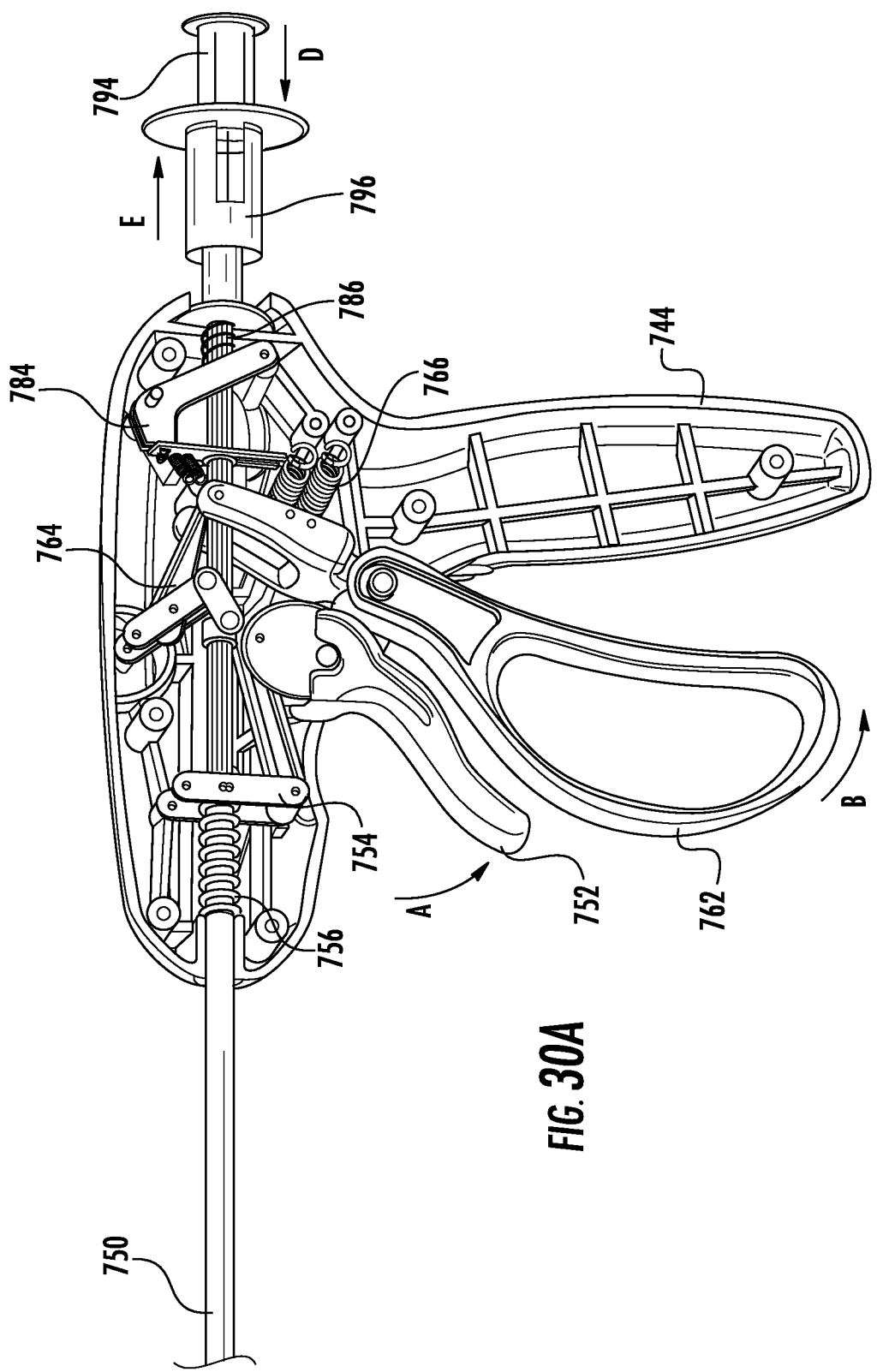
FIG. 30A is a perspective view of the proximal end of the user interface of the tissue retractor assembly of FIG. 27A with the cover of the user interface removed for clarity.
Figure 30B:
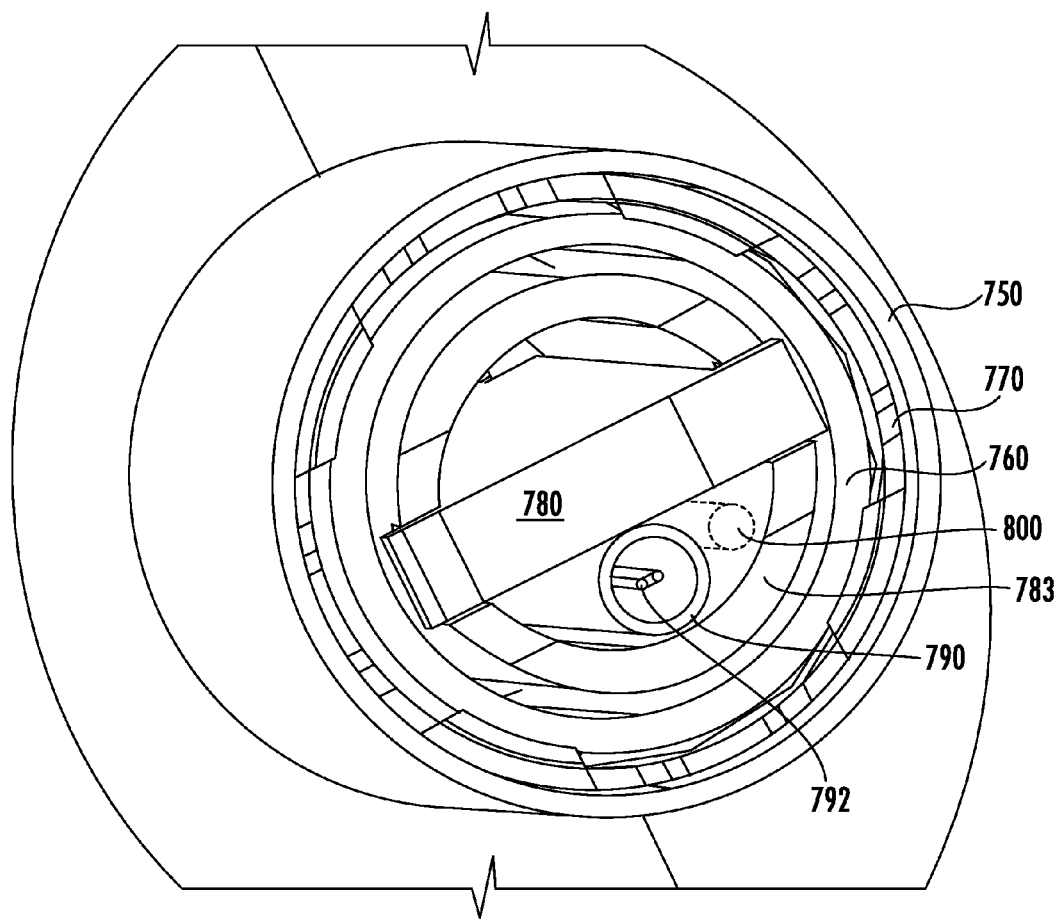
FIG. 30B is a perspective end view of the distal end of the user interface of the tissue retractor assembly of FIGS. 27A-B with the grasper and anchor removed for clarity.

All of the components of the tissue retractor assembly are controllable by the user via the universal user interface 740, depicted in perspective in FIG. 27A and with the outer cover removed for clarity in FIG. 27B. Generally, interface 740 has a distal end 741A which contacts and interacts directly with grasper 710 and anchor 730 and a proximal end 741B, of which FIG. 30A is a magnified view. FIG. 30B is a magnified end view of distal end 741A with the grasper and removed for clarity, and FIG. 30C is a sectional view of distal end 741A.

Opening and closing of grasper 710 is controlled by trigger 752, which is mechanically connected to outer cannula tube 750 via linkage 754. Trigger 752 is biased into the position shown in FIG. 30A by spring 756. When the user moves trigger 752 in the direction of arrow A in FIG. 30A (e.g., by squeezing it, using pommel 744 for opposability), linkage 754 moves outer tube 750 in a distal direction (to the left in the drawings). As described above, the distal rim of outer tube 750 abuts against bosses 719B of grasper arms 712, 714, forcing jaws 716 open. Because trigger 752 is biased by spring 756, when the user releases his grip on trigger 752, trigger 752 moves back into its original position shown in FIG. 30A, outer tube 750 moves proximally away from grasper 710, and jaws 716 re-close owing to the biasing force of coil spring 718. In this way, by squeezing and releasing trigger 752, the user can easily open and close grasper 710 to secure it on tissue or an organ to be refracted.

Deployment of anchor 730 is effectuated by operation of trigger 762, which is mechanically connected to middle cannula or tube 760 via linkage 764. Trigger 762 is biased into the position shown in FIG. 30A by spring 766. In the preferred embodiment, anchor 730 is secured to the distal end of middle tube 760 via gripper sleeve 770, to be described below. When the user moves trigger 762 in the direction of arrow B in FIG. 30A (e.g., by squeezing it, using pommel 744 for opposability), linkage 764 moves middle tube 760 in a distal direction (to the left in the drawings). Initially, anchor 730 is disposed within outer tube 750 as shown in FIG. 30C in the straight-leg configuration of FIG. 29B. As the user squeezes trigger 762, middle tube 760 pushes anchor 730 distally. As legs 738 emerge from the distal end of outer tube 750, they curl back into their natural curved configuration as shown in FIG. 29A. If the distal end of outer tube 750 is pressed against tissue such as the abdominal wall, legs 738 penetrate and hook into that tissue, firmly securing the anchor therein. When it is desired to remove anchor 730 from the abdominal wall, anchor 730 is reattached to the distal end of middle tube 760, which is pushed out of outer tube 750 by operation of trigger 762 as when the anchor is being deployed. When the anchor is resecured onto middle tube 760, the user relaxes his grip on trigger 762, and middle tube 760 withdraws into outer tube 750, pulling anchor 730 inside. The distal edge and inner surface of outer tube 750 pulls the anchor legs 738 to uncurl out of the abdominal wall tissue and into the straight configuration of FIG. 29B.

Figure 31:
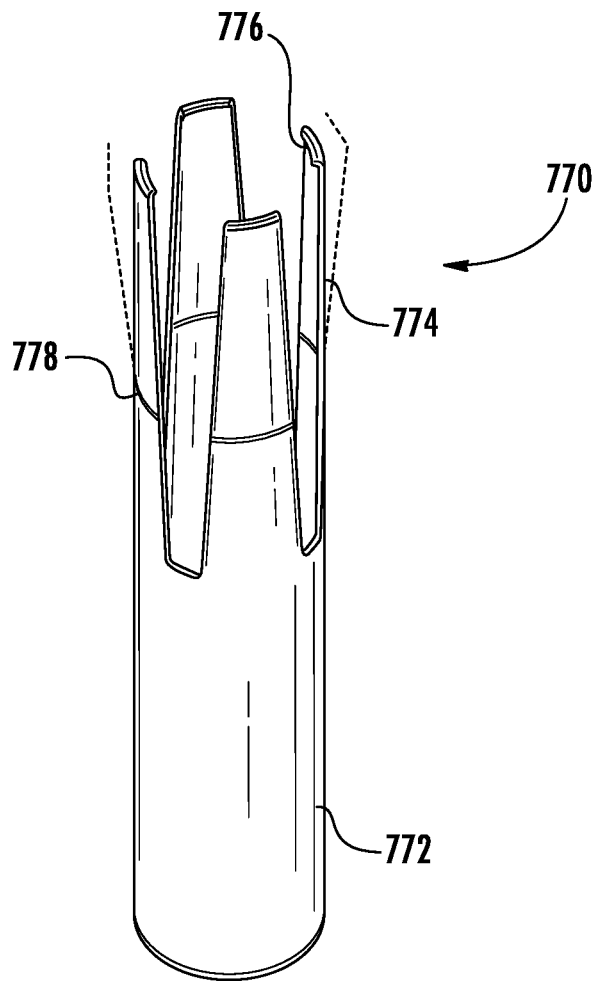
FIG. 31 is a perspective view of an anchor gripper sleeve in accordance with the invention.

The preferred structure for securing anchor 730 to middle tube 760 and for enabling positioning of the anchor in a desired location in the abdominal wall is gripper sleeve 770, shown in perspective by itself in FIG. 31 and in the overall assembly in FIGS. 30B, 30C, and 27A (in shadow). Gripper sleeve 770 is a relatively short, tubular construct having a main proximal section 772 that is preferably welded or otherwise secured to/over the distal end of middle tube 760. A plurality of arms 774 project from the distal end of gripper sleeve 770, each terminating in a substantially orthogonal tab or tooth 776 pointing inwardly. As shown in FIG. 30C, for example, teeth 776 are configured to dig into groove 734 (and/or onto flange 735) of anchor 730 to retain anchor 730 on the distal end of middle tube 760. Arms 774 are naturally biased outward, preferably at least at fold point 778, as depicted in dotted lines in FIG. 31; teeth 776 only dig into groove 734 when both the anchor and the gripper sleeve are disposed within outer tube 750. As the middle tube 760 is pushed distally out of outer tube 750 via operation of trigger 762, arms 774 bias radially outward, and teeth 776 move out of engagement from groove 734. Since legs 738 of anchor 730 are being sunk into abdominal wall tissue while this is occurring, the anchor leaves the gripping sleeve 770 and remains secured to the abdominal wall.

Thus far, description has been given as to how to open and close the grasper jaws 716 by operation of user interface 740 (specifically, trigger 752). Once the grasper is secured to the tissue to be retracted, the grasper must be freed from the overall assembly 700. In the preferred embodiment, grasper 710 is connected to user interface 740 via hook 780, best illustrated in FIGS. 30B-C. Preferably, the circular portion 718A of coil spring 718 is initially mounted on the distal end of hook 780 prior to use of the assembly 700. As the grasper jaws are opened and closed about the tissue to be retracted, grasper 710 remains secured to the distal end 741A of actuator 740 as shown in FIG. 27A, for example. At that point, as shown in FIG. 30C, hook 780 is completely within outer tube 750, and coil spring 718 is trapped between hook 780 and outer tube 750. Hook 780 is preferably disposed within inner tube 783 (see FIGS. 30B-C); inner tube 783 preferably does not move at all and keeps the orientation of hook 780 constant so as to keep the orientation of grasper 710 constant with respect to the actuator and the rest of the assembly.

Hook 780 is mechanically connected to slide knob 782 (see FIGS. 27A, 32-A-C) via linkage 784 and biased into its neutral position within outer tube 750 by spring 786. Sliding of slide knob 782 in a distal direction as shown by arrow C in FIG. 27A moves hook 780 distally so as to protrude from the distal end of outer tube 750. This motion of hook 780 pushes grasper 710 along with it, leaving grasper 710 free to be removed from hook 780 and left attached to the tissue to which its jaws 716 are secured. When the user releases his grip or pressure on knob 782, spring 786 pulls hook 780 back proximally within outer tube 750.

Preferably, the hook actuation assembly also includes a locking mechanism to prevent accidental or inadvertent movement of hook 780 out of outer tube 750, because once grasper 710 is no longer in contact with outer tube 750, jaws 716 cannot be readily controlled. As such, the hook actuation assembly also preferably includes a locking gate 787 connected to linkage 784 and spring 789A. Locking gate 787 preferably includes a locking window 788 that is dimensioned smaller than a corresponding locking flange 781 on the proximal end of hook 780. Locking gate 787 is preferably moved by the same action of slide knob 782; pushing knob 782 in a distal direction along arrow C (see FIG. 27A) serves to raise locking gate 787 off of hook 780 and thereby disengage locking window 788 from hook locking flange 781.

Figure 32C:
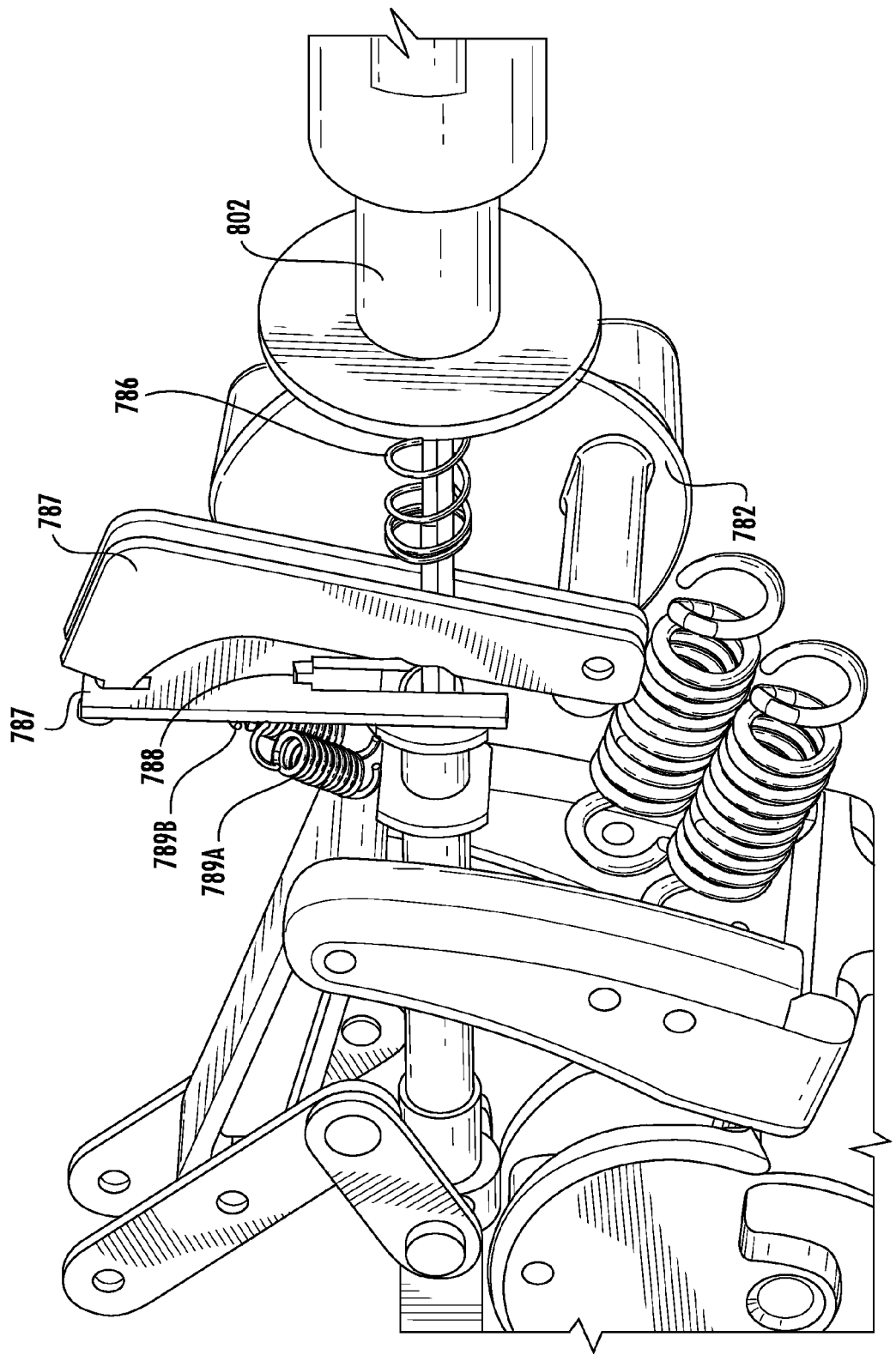

The functioning of locking gate 787 is depicted serially in FIGS. 32A-C. First, in FIG. 32A, the hook actuation assembly is in its beginning neutral configuration, with the locking window 788 of locking gate 787 engaging hook 780 at its locking flange 781. Next, in FIG. 32B, slide knob 782 has been partially pushed distally in the direction of arrow C. Locking gate 787 has risen slightly to disengage locking window 788 from locking flange 781. At this point, hook 780 is free to move distally. Next, as shown in FIG. 32C, slide knob is pushed further in the direction of arrow C, and hook 780 now projects out of the distal end of outer tube 750. Grasper 710 may be removed therefrom and set in place on the tissue to be refracted. Preferably, the user simply pushes slide knob 782 in a single smooth motion to first disengage locking gate 787 and then move hook 780 distally. However, other configurations of linkages and hook locking mechanisms are contemplated as being within the scope of the invention, e.g., a two-step motion of slide knob 782 or a similar actuator, a separate safety switch (not shown) controlling the operation of the locking gate 787 or a similar structure, and the like.

In the preferred embodiment, three springs operate to maintain the neutral position of the hook actuator assembly: spring 786 biases the hook itself backward in a proximal direction; spring 789A biases the locking gate 787 downward to engage locking flange 781 of hook 780; and spring 789B (next to spring 789A and partially obstructed by locking gate 787) is connected to the distal end of linkage 784 and biases same. The invention contemplates other convenient biasing configurations, e.g., more or fewer springs in the same or different locations, and the like.

With grasper 710 deployed on the tissue to be retracted and anchor 730 deployed in the abdominal wall, the structure that enables actual tissue retraction is the movable support, which is preferably a suture 800 (see FIG. 30B). Suture 800 is preferably disposed at a distal end within inner tube 783, either above or below hook 780. A proximal end of suture 800 is preferably wound around suture spindle 802 (see FIGS. 32A-C) and unspools as needed. The distal end of suture 800 is preferably threaded through anchor 730 and tied or otherwise secured to grasper 710 (e.g., through its coil spring 718 and through holes 717). With the user actuator 740 withdrawn from the patient's body, the clinician can retract on the tissue in grasper 710 simply by pulling on suture 800. Because suture 800 is threaded through anchor 730 which is fixed to the abdominal wall, the system acts like a pulley. The more suture 800 is pulled proximally away from the patient, the more the tissue is retracted. Thus, the invention allows for dynamic (i.e., variable and real-time) selection of how much retraction to provide to a tissue.

At some point at the close of a procedure, the user will likely wish to retrieve the various implements secured within the patient. One could use the separate anchor retrieval tool 600 described above; however in the preferred assembly 700, the tool retrieval mechanism is incorporated and integral with user interface 740.

Specifically, disposed in conduit 790 within stationary inner tube 783 is provided a wire loop 792 (see FIGS. 30B-C). The distal end of wire loop 792 is selectively projectable out of the distal end of outer tube 750 via user actuation of button 794, which is attached to the proximal end of wire loop 792. A stiffening structure (not shown) may be provided around part or all of wire loop 792 to provide stability and prevent wire loop 792 from twisting or getting stuck on itself in any way. Depressing button 794 in the direction of arrow D (see FIG. 30A) directly pushes wire loop 792 out of the distal ends of inner tube 783 and outer tube 750. The clinician can then thread suture 800 through the exposed wire loop and then release button 794. Preferably, button 794 is spring biased in a direction opposite to arrow D by a spring (not shown); as such, wire loop 792 will withdraw back into inner tube 783 when button 794 is released, trapping suture 800 therein. The clinician can then follow suture 800 down to anchor 730 and retrieve anchor 730 with gripping sleeve 770. Once anchor 730 is retrieved, the clinician can continue to follow suture 800 down to grasper 710 until the proximal end of grasper 710 abuts against the distal edge of outer tube 750, causing grasper jaws 716 to open and release the retracted tissue. Knob 796 is then withdrawn proximally in the direction of arrow E (see FIG. 30A), and the entire assembly is removed from the patient.

Figure 33A:
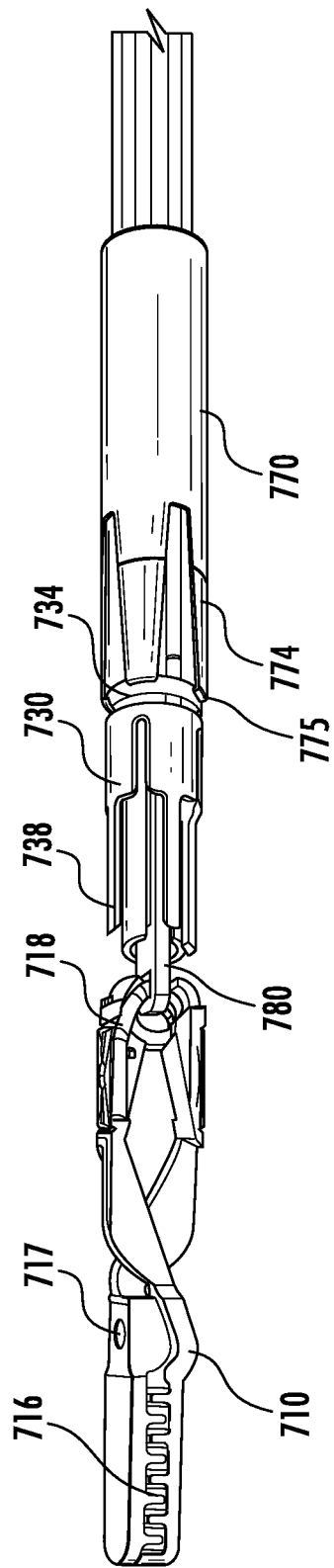
FIGS. 33A-G are a series of perspective views of the distal end of the tissue retractor assembly of FIGS. 27A-B as it is used in operation.

In operation, tissue retractor assembly 700 is used as follows and as depicted in FIGS. 33A-G (with outer tube 750 removed for clarity in FIG. 33A). In FIG. 33A, assembly 700 is in its pre-use configuration: grasper jaws 716 are closed, and grasper 710 is secured onto hook 780 just within the distal end of outer tube 750. Hook 780 is biased proximally so that the proximal end of grasper 710 abuts against the distal rim of outer tube 750, preferably with narrower section 719A being disposed within outer tube 750 and wider bosses 719B being disposed abutting the distal rim thereof. A suture (not shown in FIG. 33A) is threaded through holes 717 in grasper arms 712, 714. Anchor 730 is secured within outer tube 750 via teeth 776 of arms 774 of gripper sleeve 770, which is substantially entirely contained within outer tube 750. The user grasps universal user interface 740 in a hand, preferably with pommel 744 in the palm of his hand like a pistol.

Figure 33B:
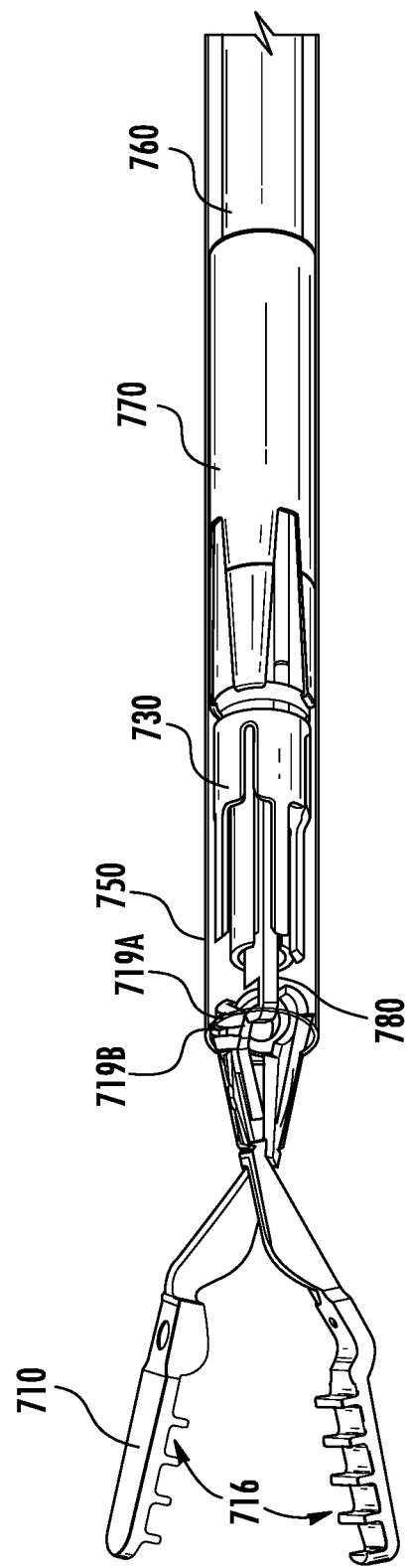
Figure 33C:
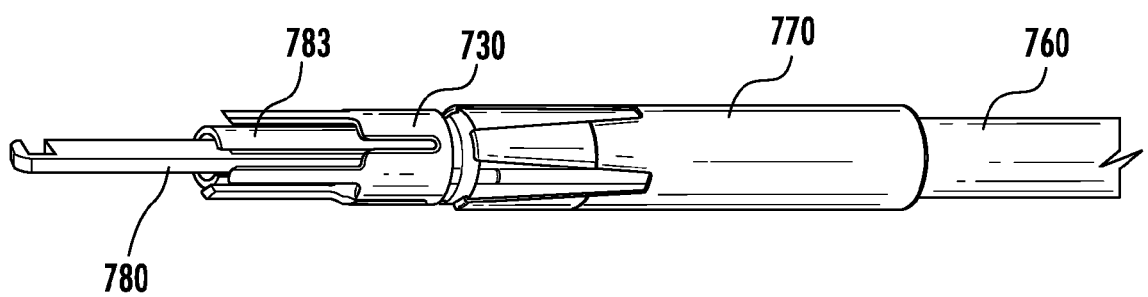

Upon selecting a tissue, organ, or other bodily structure to retract, the user positions grasper 710 at or near the tissue to be retracted. As shown in FIG. 30A, the user squeezes trigger 752 in the direction of arrow A, preferably using pommel 744 for opposability. Linkage 754 transmits the force from trigger 752 to outer tube 750 to move outer tube 750 distally. Since, as described above and as shown in FIG. 28C, bosses 719B abut against the distal rim of outer tube 750, distal movement of the outer tube 750 pushes the tube against bosses 719B, which forces open the jaws 716 of grasper 710 as shown in FIG. 33B (with the outer tube 750 made transparent for clarity). The user can secure the grasper jaws 716 around the desired tissue and then release trigger 752. Owing to the biasing force of spring 756, trigger 752 and outer tube 750 will return to their original positions, and jaws 716 will close securely around the tissue to be retracted.

Next, the user must free grasper 710 from user interface 740. To do so, the user slides slide knob 782 in the direction of arrow C (see FIG. 27A). This serves to unlock locking gate 787 from hook 780 and push hook 780 distally out of the end of outer tube 750. With the jaws of the grasper secured to the to-be-retracted tissue, a slight lateral motion frees the grasper coil spring 718 from hook 780, and the distal end of the assembly is configured as in FIG. 33C.

Figure 33D:
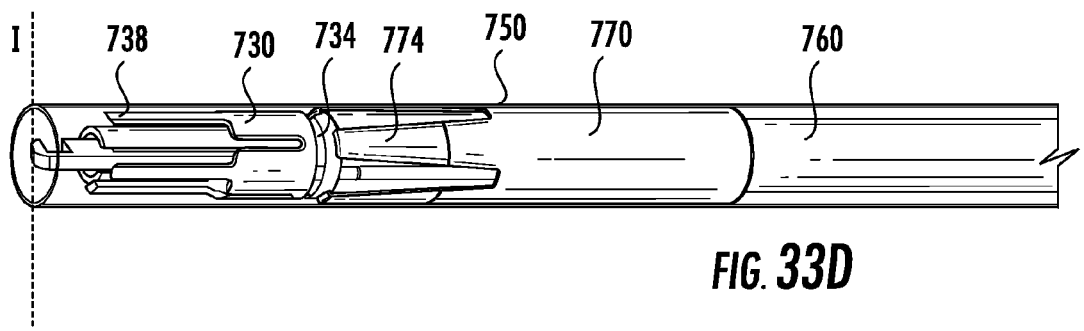
Figure 33E:
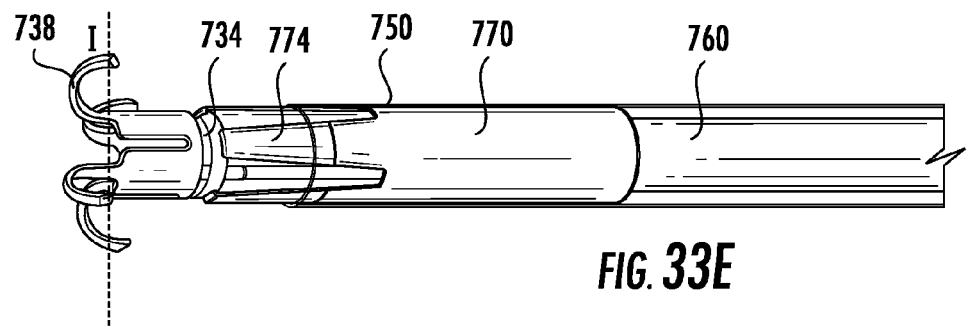
Figure 33F:
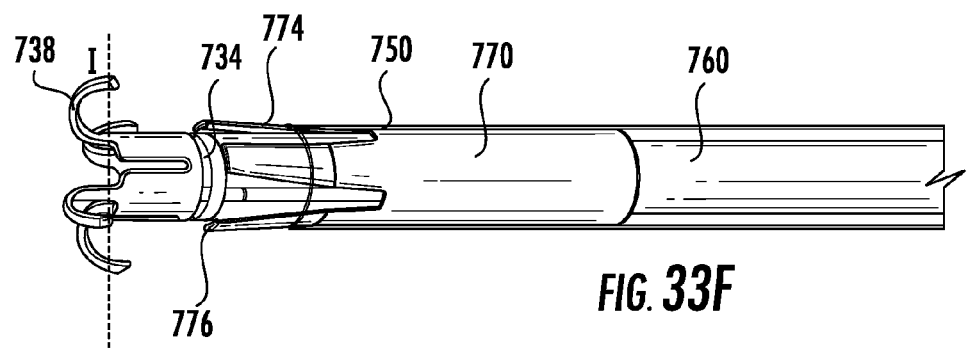

The user must then deploy anchor 730 into the abdominal wall or a similarly suitable anatomical structure. The device begins the anchor deployment as shown in FIG. 33D with the distal end of outer tube 750 pressed against the tissue T. Then, the user squeezes trigger 762 in the direction of arrow B (see FIG. 30A), which (through linkage 764) causes middle tube 760 to move distally. As middle tube 760 moves distally and anchor 730 leaves the confines of outer tube 750, legs 738 gently penetrate tissue T and return to their naturally radially outwardly curved configuration as shown in FIG. 33E. The user completes the stroke of trigger 762, and arms 774 of gripper sleeve 770 naturally return to their radially outwardly biased configuration as shown in FIG. 33F. As a result, gripper sleeve teeth 776 disengage from anchor groove 734, and the anchor remains firmly implanted within tissue T. Assembly 700 may then be withdrawn from the patient, and the suture 800 can be manipulated to provide greater or lesser retraction of the tissue secured in grasper jaws 716 as desired.

At the conclusion of the procedure, the user preferably must locate the anchor and grasper for removal. First, button 794 is depressed in the direction of arrow D (see FIG. 30A) so as to extend wire loop 792 out of conduit 790 and thence out of outer tube 750. Suture 800 is threaded through wire loop 792, and button 794 is released, causing wire loop 792 to be withdrawn, trapping suture 800 within conduit 790. The distal end 741 of user interface 740 is then reinserted into the patient so as to locate the various components still attached to the distal end of suture 800.

Figure 33G:
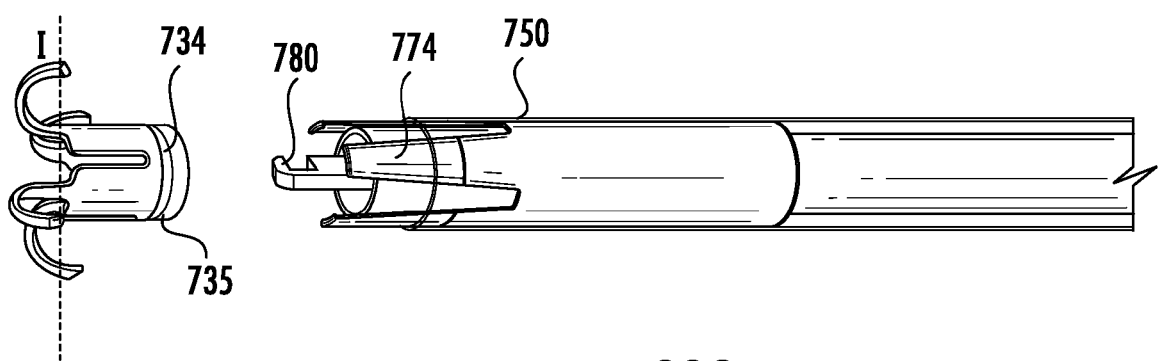

The first stop along suture 800 is anchor 730. As shown in FIG. 33G, the user may extend hook 780 to assist in finding anchor 730 as hook 780 fits within main body 732 of anchor 730. Hook 780 helps align anchor 730 with the distal end 741 of user interface 740. Thereafter, the user squeezes trigger 762 to extend middle tube 760 and thus extend gripper sleeve 770. As gripper sleeve 770 is extended, its arms 774 bias radially outwardly to be able teeth 776 to dig into anchor groove 734 and/or onto anchor flange 735. The user relaxes his grip on trigger 762, and middle tube 760 is withdrawn into outer tube 750, first causing arms 774 to cinch around anchor groove 734/flange 735, then pulling anchor 730 proximally out of tissue T. Anchor legs 738 eventually straighten out within outer tube 750.

Next, the user follows suture 800 along to grasper 710. The user extends hook 780 by operation of slide knob 782 in the direction of arrow C (FIG. 27A). The user secures hook 780 within grasper coil spring 718, and then releases slide knob 782. Spring 786 withdraws hook 780 back inside outer tube 750 with the proximal end of grasper 710 abutting against the distal rim of outer tube 750. The user then squeezes trigger 752 to move outer tube 750 distally, thereby pushing against bosses 719B of grasper 710, forcing open jaws 716 and releasing the retracted tissue therefrom. Trigger 752 is released, and jaws 716 close. With the grasper free of the tissue and secured to the distal end of user interface 740, the entire device is removed from the patient.

The invention is not limited to the above description. For example, in nearly every circumstance where parts are biased into a given position or configuration, a coil spring is shown. However, leaf springs or any other biasing mechanisms may be employed to the convenience and ease of the manufacturer. Additionally, although the figures depict a specific configuration of linkages and mechanical connections between the various moving parts of the device and the user actuators, other connections are also contemplated. It is contemplated also that the preferred tissue retractor assembly of FIGS. 27-33 can be used with any of the embodiments depicted in FIGS. 1-26. Additionally, as described above, the hook that secures the grasper to the user interface is preferably secured through the coil spring of the grasper. However, the hook could be secured to another structure on the grasper, and the grasper could be provided with an additional structure for this purpose.

Having described certain embodiments of the invention, it should be understood that the invention is not limited to the above description or the attached exemplary drawings. Rather, the scope of the invention is defined by the claims appearing hereinbelow and includes any equivalents thereof as would be appreciated by one of ordinary skill in the art.

What is claimed is:

1. An intracorporeal surgical tissue retractor, comprising:
   a) an anchor selectively deployable in a first tissue not to be retracted;
   b) a grasper selectively deployable on a second tissue to be retracted;
   c) a longitudinally selectively movable support threadable through said anchor and attached at a substantially distal end of said movable support to said grasper; and
   d) a deployment user interface, couplable to said movable support and having a proximal end manipulable by a user extracorporeally and a distal end releasably attachable to both said anchor and said grasper, adapted to intracorporeally deploy said anchor into the first tissue and said grasper onto the second tissue;
   said anchor comprising a plurality of distally projecting legs, and a substantially proximally disposed main body;
   said legs of said anchor being curved outwardly and made from a resilient material;
   said user interface further comprising an outer cannula and an anchor positioning tool being attached to the distal end of said user interface and relatively withdrawable inside of a distal end of said outer cannula,
   wherein as said anchor positioning tool is relatively withdrawn into said outer cannula, said outer cannula urges said legs of said anchor that is releasably secured to said anchor positioning tool into a substantially straight configuration.

2. An intracorporeal surgical tissue retractor according to claim 1, wherein when said legs are in said substantially straight configuration, said anchor is deployable into a tissue not to be retracted.

3. An intracorporeal surgical tissue retractor according to claim 1, said user interface further comprising a first actuator, disposed on said proximal end of said user interface and mechanically coupled to said anchor positioning tool, enabling selective longitudinal movement of said anchor positioning tool and deployment of said anchor in the first tissue.

4. An intracorporeal surgical tissue retractor according to claim 3, said user interface further comprising a substantially immovable grip for opposability of movement of said first actuator.

5. An intracorporeal surgical tissue retractor according to claim 1, wherein said resilient material of said anchor is variably pliant at different temperatures, wherein said material is less pliant at body temperature than at room temperature.

6. An intracorporeal surgical tissue retractor, comprising:
a) an anchor selectively deployable in a first tissue not to be retracted;
b) a grasper selectively deployable on a second tissue to be retracted;
c) a longitudinally selectively movable support threadable through said anchor and attached at a substantially distal end of said movable support to said grasper; and
d) a deployment user interface, couplable to said movable support and having a proximal end manipulable by a user extracorporeally and a distal end releasably attachable to both said anchor and said grasper, adapted to intracorporeally deploy said anchor into the first tissue and said grasper onto the second tissue;
said anchor comprising a plurality of distally projecting legs, and a substantially proximally disposed main body;
further comprising an anchor positioning tool attachable to said distal end of said user interface and releasably attachable to said main body of said anchor; and
wherein one of said main body of said anchor and said anchor positioning tool comprises a flange and the other of said main body of said anchor and said anchor positioning tool comprises a plurality of arms releasably securable to said flange.

7. An intracorporeal surgical tissue retractor according to claim 6, said user interface comprising an outer cannula and a middle cannula disposed within said outer cannula, said anchor positioning tool being attached to a distal end of said middle cannula.

8. An intracorporeal surgical tissue retractor according to claim 7, said arms being disposed on said anchor positioning tool and biased radially outwardly from said middle cannula, wherein when said middle cannula is relatively withdrawn into said outer cannula, said arms are urged radially inwardly via said outer cannula.

9. An intracorporeal surgical tissue retractor according to claim 8, said legs of said anchor being curved outwardly and made from a resilient shape memory material, wherein as said middle cannula is relatively withdrawn into said outer cannula, said outer cannula urges said legs of said anchor into a substantially straight configuration.

10. An intracorporeal surgical tissue retractor according to claim 9, said proximal end of said user interface comprising a first actuator coupled to said middle cannula, wherein actuating of said first actuator in a first motion moves said middle cannula in a distal direction to enable deployment of said anchor in the first tissue.

11. An intracorporeal surgical tissue retractor according to claim 10, wherein actuating said first actuator in a second motion moves said middle cannula in a proximal direction to withdraw said anchor from the first tissue.

12. An intracorporeal surgical tissue retractor, comprising:
a) an anchor selectively deployable in a first tissue not to be retracted;
b) a grasper selectively deployable on a second tissue to be retracted;
c) a longitudinally selectively movable support threadable through said anchor and attached at a substantially distal end of said movable support to said grasper; and
d) a deployment user interface, couplable to said movable support and having a proximal end manipulable by a user extracorporeally and a distal end releasably attachable to both said anchor and said grasper, adapted to intracorporeally deploy said anchor into the first tissue and said grasper onto the second tissue;
wherein when said anchor is deployed in the first tissue, said grasper is deployed on the second tissue, and said movable support is selectively moved proximally, the second tissue is selectively retracted;
a main body of said anchor further comprising a shoulder region releasably attachable to an anchor positioning tool attached to said distal end of said user interface.

13. An intracorporeal surgical tissue retractor according to claim 12, said shoulder region comprising a groove and said anchor positioning tool comprising a plurality of arms releasably securable in said groove.

14. An intracorporeal surgical tissue retractor according to claim 13, said user interface comprising an outer cannula and a middle cannula disposed within said outer cannula, said anchor positioning tool being attached to a distal end of said middle cannula.

15. An intracorporeal surgical tissue retractor according to claim 14, said arms being biased radially outwardly from said middle cannula, wherein when said middle cannula is relatively withdrawn into said outer cannula, said arms are urged radially inwardly via said outer cannula to engage with said groove of said anchor.

16. An intracorporeal surgical tissue retractor, comprising:
a) an anchor selectively deployable in a first tissue not to be retracted;
b) a grasper selectively deployable on a second tissue to be retracted;
c) a longitudinally selectively movable support threadable through said anchor and attached at a substantially distal end of said movable support to said grasper; and
d) a deployment user interface, couplable to said movable support and having a proximal end manipulable by a user extracorporeally and a distal end releasably attachable to both said anchor and said grasper, adapted to intracorporeally deploy said anchor into the first tissue and said grasper onto the second tissue;
said grasper comprising a pair of arms forming at their respective distal ends a pair of jaws, said jaws adapted to securely attach to the second tissue, and a biasing mechanism attached to said arms biasing said jaws into a closed position;
said user interface comprising an outer cannula having a distal rim and said grasper having a proximal end at least partially abuttable against said distal rim of said outer cannula;
wherein when at least one of said outer cannula and said grasper is moved relative to the other of said outer cannula and said grasper, said distal rim of said outer cannula bears against said proximal end of said grasper and forces said jaws open opposing said biasing mechanism.

17. An intracorporeal surgical tissue retractor according to claim 16, said proximal end of said grasper having an outer diameter portion that is abuttable against said distal rim of said outer cannula, wherein relative movement of said grasper to said outer cannula forces said jaws open via abutment of said distal rim against said outer diameter portion.

18. An intracorporeal surgical tissue retractor according to claim 16, said user interface further comprising a second actuator, disposed on said proximal end of said user interface and mechanically coupled to one of said outer cannula or said grasper, enabling selective relative longitudinal movement of said grasper with respect to said outer cannula to selectively open and close said jaws of said grasper.

19. An intracorporeal surgical tissue retractor according to claim 18, further comprising a third actuator, disposed on said proximal end of said user interface and mechanically coupled to said grasper support enabling selective longitudinal movement of said grasper support to free said grasper of said user interface and to deploy said grasper onto the second tissue.

20. An intracorporeal surgical tissue retractor according to claim 19, wherein said biasing mechanism of said grasper comprises a coil spring disposed at said proximal end of said grasper and said grasper support comprising a hook formed at a distal end of said grasper support that is hookable through said coil spring.

21. An intracorporeal surgical tissue retractor according to claim 20, wherein said hook is dimensioned to fit within a main body of said anchor to facilitate retrieval of a deployed said anchor.

22. An intracorporeal surgical tissue retractor according to claim 18, said user interface further comprising a substantially immovable grip for opposability of movement of said second actuator.

23. An intracorporeal surgical tissue retractor, comprising:
   a) an anchor selectively deployable in a first tissue not to be retracted;
   b) a grasper selectively deployable on a second tissue to be retracted;
   c) a longitudinally selectively movable support threadable through said anchor and attached at a substantially distal end of said movable support to said grasper;
   d) a deployment user interface, couplable to said movable support and having a proximal end manipulable by a user extracorporeally and a distal end releasably attachable to both said anchor and said grasper, adapted to intracorporeally deploy said anchor into the first tissue and said grasper onto the second tissue;
   an anchor retrieval tool having a main body and a central shaft disposed within said main body, said central shaft having a proximal end and a distal end, said distal end of said central shaft including a sloped portion terminating in a shoulder matingly engageable with at least one flexible detent tab cut into and angled inwardly towards a center of a main body of said anchor, and
   wherein when said distal end of said central shaft enters an interior of said main body of said anchor, said tab catches underneath said shoulder of said central shaft, thereby preventing removal of said anchor from said distal end of said central shaft and thereby facilitating retrieval of said anchor from said first tissue.

24. An intracorporeal surgical tissue retractor according to claim 23, said anchor retrieval tool further comprising a locator loop projecting from a distal end of said main body of said tool, said locator loop being loopable around said movable support threaded through said anchor so that said retrieval tool is guidable along said movable support directly to said anchor.

25. An intracorporeal surgical tissue retractor according to claim 24, said locator loop being coupled to a loop tightener adapted to selectively tighten said locator loop around said movable support.

* * * * *